(12) United States Patent
Hunter et al.

(10) Patent No.: US 6,476,067 B1
(45) Date of Patent: Nov. 5, 2002

(54) N-FORMYL HYDROXYLAMINE DERIVATIVES AS ANTIBACTERIAL AGENTS

(75) Inventors: Michael George Hunter, Oxford (GB); Raymond Paul Beckett, Oxford (GB); Martin John Clements, Oxford (GB); Mark Whittaker, Oxford (GB)

(73) Assignee: British Biotech, Oxford (GB)

( * ) Notice: Subject to any disclaimer, the term of this patent is extended or adjusted under 35 U.S.C. 154(b) by 0 days.

(21) Appl. No.: 09/868,076

(22) PCT Filed: Dec. 13, 1999

(86) PCT No.: PCT/GB99/04217

§ 371 (c)(1), (2), (4) Date: Jun. 14, 2001

(87) PCT Pub. No.: WO00/35440

PCT Pub. Date: Jun. 22, 2000

(30) Foreign Application Priority Data

Dec. 16, 1998 (GB) .............................................. 9827805

(51) Int. Cl.⁷ ....................... A61K 31/27; A61K 31/445
(52) U.S. Cl. ....................................... 514/490; 514/327
(58) Field of Search ................................... 514/490, 327

(56) References Cited

U.S. PATENT DOCUMENTS 4,738,803 A * 4/1988 Roques et al. ....... 260/500.5 H

FOREIGN PATENT DOCUMENTS

| WO | 97/03783 | 2/1997 |
| WO | 97/38705 | 10/1997 |

OTHER PUBLICATIONS

Y. Jin et al: "Inhibition stereochemistry of hydroxamate inhibitors for thermolysin", Bioorganic & Medicinal Chemistry Letters, GB, Oxford, vol. 8, No. 24, 1998, pp. 3515–3518, XP002106374.

Fournie–Zalusmi M–C et al.: "New bidentases as full inhibitors of enkephalin–degrading enzymes: synthesis and analgesis properties" Journal of Medicinal Chemistry, US American Chemical Society, Washington, vol. 28, No. 9, Jan. 1, 1985, pp. 1158–1169, XP002019770.

Mazel, D., et al.: "Genetic characterization of polypeptide deformylase, a distinctive enzyme of eubacterial translation", Embo Journal, GB, Oxford University Press, Surrey, vol. 13, No. 4, Feb. 15, 1994, pp. 914–923, XP002043973.

P. T. Ravi Rajagopalan, et al.: "Peptide Deformylase: A new type of mononuclear iron protein", Journal of the American Chemical Society, US, American Chemical Society, Washington, D.C., vol. 119, No. 119, 1997, pp. 12418–12419, XP002106376.

* cited by examiner

Primary Examiner—Kevin E. Weddington
(74) Attorney, Agent, or Firm—Banner & Witcoff LLP

(57) ABSTRACT

Compounds of formula (I) are in the preparation of antibacterial agents, wherein: $R_1$ represents hydrogen, $C_1$–$C_6$ alkyl or $C_1$–$C_6$ alkyl substituted by one or more halogen atoms; $R_2$ represents a group $R_{10}(X)_n$—(ALK)— wherein $R_{10}$ represents hydrogen, a $C_1$–$C_6$ alkyl, $C_2$–$C_6$ alkenyl, $C_1$–$C_6$ alkynyl, cycloalkyl, aryl, or heterocyclyl group, any of which may be unsubstituted or substituted by ($C_1$–$C_6$)alkyl, ($C_1$–$C_6$)alkoyy, hydroxy, mercapto, ($C_1$–$C_6$)alkylthio, amino, halo, trifluoromethyl, cyano, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group, and ALK represents a straight or branched divalent $C_1$–$C_6$ alkylene, $C_2$–$C_6$ alkenylene, or $C_2$–$C_6$ alkynylene radical, which may be interrupted by one or more non-adjacent —NH—, —O— or —S— linkages, X represents —NH—, —O— or —S—, and n is 0 or 1, R represents hydrogen or $C_1$–$C_6$ alkyl, $R_3$ represents the characterising group or a natural or non-natural α amino acid in which any functional groups may be protected; and $R_4$ represents an ester or thioester group.

15 Claims, No Drawings

N-FORMYL HYDROXYLAMINE DERIVATIVES AS ANTIBACTERIAL AGENTS

This invention relates to the use of N-formyl hydroxylamine derivatives as antibacterial agent

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penidillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolvedlarisen which makes them particularly difficult to eradicate. Examples of such strains are methicillin resistant *Staphylococcus aureus* (MRSA), methicillin resistant coagulase negative Staphylococci (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus*, is of utmost importance.

BRIEF DESCRIPTION OF THE INVENTION

This invention is based on the finding that certain hydroxamic acid and N-formyl hydroxylamine derivatives have antibacterial activity, and makes available a new class of antibacterial agents. The inventors have found that the compounds with which this invention is concerned are antibacterial with respect to a range of Gram-positive and Gram-negative organisms.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes the methionyl moiety carried by the initiator tRNA is N-formylated prior to its incorporation into a polypeptide. Consequently, N-formylmethionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:939–49, 1997), it has no eukaryotic counterpart, making it an attractive target for antibacterial chemotherapy.

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280:515–23, 1998). The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Biol. 5:1053–8, 1998; Becker et al., J. Biol. Chem. 273:11413–6, 1998; Hao et al., Biochemistry, 38:4712–9, 1999; Dardel et al., J. Mol. Biol. 280:501–13, 1998; O'Connell et al., J. Biomol. NMR, 13:311–24, 1999), indicating similarities in active site geometry to metalloproteinases such as thermolysin and the metzincins.

Recently the substrate specificity of PDF has been extensively studied (Ragusa et al., J. Mol. Biol. 289:1445–57, 1999; Hu et al., Biochemistry 38:643–50, 1999; Meinnel et al., Biochemistry, 38:4287–95, 1999). These authors conclude that an unbranched hydrophobic chain is preferred at P1', while a wide variety of P2' substituents are acceptable and an aromatic substituent may be advantageous at the P3' position. There have also been reports that small peptidic compounds containing an H-phosphonate (Hu et al., Bioorg. Med. Chem. Lett., 8:2479–82, 1998) or thiol (Meinnel et al., Biochemistry, 38:4287–95, 1999) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367:297–302, 1999). However, the identity of the metal binding group and its spacing from the rest of the molecule ("recognition fragment") has not been studied extensively. Furthermore, non-peptidic PDF inhibitors, which may be desirable from the point of view of bacterial cell wall permeability or oral bioavailability in the host species, have not been identified.

RELATED PRIOR ART

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis. That prior art does not disclose or imply that N-formyl hydroxylamine derivatives have antibacterial activity.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors. This prior art does not disclose or imply that N-formyl hydroxylamine derivatives have antibacterial activity either.

Our copending Intentional Patent Application No. WO 99/39704 describes and claims, inter alia, the use of a compound of formula (I) or a pharmaceutically or veterinarily acceptable salt thereof in the preparation of an antibacterial composition:

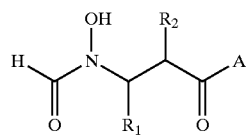

(I)

wherein $R_1$ represents hydrogen, $C_1$–$C_6$ alkyl or $C_1$–$C_6$ alkyl substituted by one or more halogen atoms; $R_2$ represents a substituted or unsubstituted $C_1$–$C_6$ alkyl, cycloalkyl ($C_1$–$C_6$ alkyl)— or aryl($C_1$–$C_6$ alkyl)— group; and A represents a group of formula (IA), or (IB):

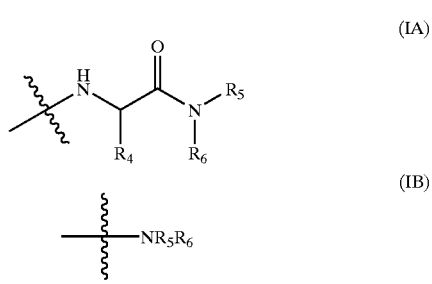

wherein $R_4$ represents the side chain of a natural or non-natural alpha amino acid, and $R_5$ and $R_6$ when taken together with the nitrogen atom to which they are attached form an optionally substituted saturated heterocyclic ring of 3 to 8 atoms which ring is optionally fused to a carbocyclic or second heterocyclic ring.

Very many hydroxamic acid derivatives are known. Many have been disclosed as having matrix metalloproteinase (MMP) inhibitory activity, and thus to be potentially useful for the treatment of diseases mediated by MMPs, for example cancer, arthritides, and conditions involving tissue remodeling such as wound healing, and restenosis. In addition our International Patent Application No. PCT/GB99/01541 describes the use of analogues of the N-formylhydroxylamine derivatives of WO 99/39704 (wherein the N-formylhydroxylamine group is replaced by a hydroxamic acid group) in the preparation of an antibacterial composition.

DETAILED DESCRIPTION OF THE INVENTION

According to the first aspect of the present invention there is provided the use of a compound of formula (I) or a pharmaceutically or veterinarily acceptable salt, hydrate or solvate thereof in the preparation of an antibacterial composition:

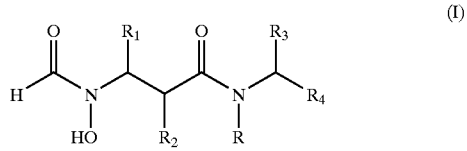

(I)

wherein:

$R_1$, represents hydrogen, $C_1$–$C_6$ alkyl or $C_1$–$C_6$ alkyl substituted by one or more halogen;

$R_2$ represents a group $R_{10}$—(X)$_n$—(ALK)— wherein
$R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), trifluoromethyl, cyano, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group, and ALK represents a straight or branched divalent $C_1$–$C_6$ alkylene, $C_2$–$C_6$ alkenylene, $C_2$–$C_6$ alkynylene radical, and may be interrupted by one or more non-adjacent —NH—, —O— or —S— linkages, X represents —NH—, —O— or —S—, and
n is 0 or 1;
R represents hydrogen or $C_1$–$C_6$ alkyl,
$R_3$ represents the characterising group of a natural or non-natural a amino acid in which any functional groups may be protected; and
$R_4$ represents an ester or thioester group,
or a pharmaceutically acceptable salt, hydrate or solvate thereof.

In another aspect, the invention provides a method for the treatment of bacterial infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above.

In a further aspect of the invention there is provided a pharmaceutical or veterinary composition comprising a compound as defined by reference to formula (I) above, together with a pharmaceutically or veterinarily acceptable excipient or carrier.

Compositions of the invention may additionally include an antibacterial agent other than one defined by reference to formula (I) above.

In addition to their pharmaceutical or veterinary use, the compounds of the invention may also be of use as component(s) of general antibacterial cleaning or disinfecting materials.

According to a preferred embodiment, the various aspects of the invention can be applied against "β-lactam"-resistant bacteria and the infections they cause.

As defined herein, "β-lactam"-resistant bacteria are those bacteria that are resistant to antibiotics characterised by the presence of a β-lactam ring. Such compounds are more commonly known in the art as members of the penicillin or cephalosporin families of compounds. Methicillin-resistant *Staphylococcus aureus* is an example of a "β-lactam"-resistant bacterium (also referred to herein as β-lactam antibiotic-resistant bacterium).

As used herein the term "($C_1$–$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$–$C_6$)alkylene radical" means a saturated hydrocarbon chain having from 1 to 6 carbon atoms and two unsatisfied valencies.

As used herein the term "($C_2$–$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent ($C_2$–$C_6$)alkenylene radical" means a hydrocarbon chain having from 2 to 6 carbon atoms, at least one double bond, and two unsatisfied valencies.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_2$–$C_6$)alkynylene radical" means a hydrocarbon chain having from 2 to 6 carbon atoms, at least one triple bond, and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms, and optionally fused to a benzyl or pyridyl ring; and to groups consisting of two covalently linked 5- or 6- membered aromatic rings each containing one or more heteroatoms; and to groups consisting of a monocyclic carbocyclic aromatic group covalently linked to a 5- or 6-membered aromatic rings containing one or more heteroatoms;. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "heterocyclyl" or "heterocyclic" includes "heteroaryl" as defined above, and in particular means a 5–7 membered aromatic or non-armoatic heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

The term "ester" or "esterified carboxyl group" means a group $R_9O(C=O)$— in which $R_9$ is the group characterising the ester, notionally derived from the alcohol $R_9OH$.

The term "thioester" means a group $R_9S(C=O)$— or $R_9S(C=S)$— or $R_9O(C=S)$— in which $R_9$ is the group characterising the thioester, notionally derived from the alcohol $R_9OH$ or the thioalcohol $R_9SH$.

Unless otherwise specified in the context in which it occurs, the term "substituted" as applied to any moiety herein means substituted with up to four substituents, each of which independently may be ($C_1$–$C_6$)alkyl, ($C_1$–$C_6$) alkoxy, phenoxy, hydroxy, mercapto, ($C_1$–$C_6$)alkylthio, amino, halo (including fluoro, chloro, bromo and iodo), trifluoromethyl, nitro, —COOH, —CONH$_2$. —COOR$^A$, —NHCOR$^A$, —CONHR$^A$, —NHR$^A$, —NR$^A$R$^B$, or —CONR$^A$R$_B$ wherein R$_A$ and R$_B$ are independently a ($C_1$–$C_6$)alkyl group.

As used herein the terms "side chain of a natural alpha-amino acid" and "side chain of a non-natural alpha-amino acid" mean the group R$^x$ in respectively a natural and non-natural amino acid of formula $NH_2$—$CH(R^x)$—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. For example, carboxyl groups may be esterified (for example as a $C_1$–$C_6$ alkyl ester), amino groups may be converted to amides (for example as a NHCOC$_1$–C$_6$ alkyl amide) or carbamates (for example as an NHC(=O)OC$_1$–C$_6$ alkyl or NHC(=O)OCH$_2$Ph carbamate), hydroxyl groups may be converted to ethers (for example an OC$_1$–C$_6$ alkyl or a O(C$_1$–C$_6$ alkyl) phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

There are several actual or potential chiral centres in the compounds according to the invention because of the presence of asymmetric carbon atoms. The presence of several asymmetric carbon atoms gives rise to a number of diastereomers with R or S stereochemistry at each chiral centre. The invention includes all such diastereomers and mixtures thereof. Presently it is preferred that the stereochemical configuration at the carbon atom carrying the $R_2$ group is R, and the configuration of the carbon atom carrying the $R_3$ group is S.

In the compounds for use according to the invention and in the novel compounds of the invention:

$R_1$ may be, for example, hydrogen, methyl, or trifuoromethyl. Hydrogen is currently preferred.

$R_2$ may be, for example:

$C_1$–$C_6$ alkyl, $C_3$–$C_6$ alkenyl or $C_3$–$C_6$ alkynyl;

phenyl($C_1$–$C_6$ alkyl—, phenyl($C_3$–$C_6$ alkenyl)— or phenyl($C_3$–$C_6$ alkynyl)-optionally substituted in the phenyl ring;

cycloalkyl($C_1$–$C_6$ alkyl)-, cycloalkyl($C_3$–$C_6$ alkenyl)- or cycloalkyl($C_3$–$C_6$ alkynyl)-optionally substituted in the phenyl ring;

heterocyclyl($C_1$–$C_6$ alkyl)-, heterocyclyl($C_3$–$C_6$ alkenyl)- or heterocyclyl($C_3$–$C_6$ alkynyl)- optionally substituted in the heterocyclyl ring;

4-phenylphenyl($C_1$–$C_6$ alkyl)-, 4-phenylphenyl($C_3$–$C_6$ alkenyl)-, 4-phenylphenyl($C_3$–$C_6$ alkynyl)-, 4-heteroarylphenyl($C_3$–$C_6$ alkyl)-, 4-heteroarylphenyl($C_3$–$C_6$ alkenyl)-, 4-heteroarylphenyl($C_3$–$C_6$ alkynyl)-, optionally substituted in the terminal phenyl or heteroaryl ring;

Specific examples of such groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl) prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are n-propyl, n-butyl, n-pentyl, benzyl and cyclopentylmethyl R may be, for example, hydrogen or methyl, with hydrogen being presently preferred.

$R_3$ may be, for example $C_1$–$C_6$ alkyl, phenyl, 2,-3-, or 4-hydroxyphenyl, 2,-3-, or 4-methoxyphenyl, 2,-3-, or 4-pyridylmethyl, 2,-3-, or 4-hydroxybenzyl, 2,-3-, or 4-benzyloxybenzyl, 2,-3-, or 4-$C_1$–$C_6$, alkoxybenzyl, or benzyloxy($C_1$–$C_6$alkyl)-group; or the characterising group of a natural α amino acid, for example benzyl, iso-propyl, isobutyl, methyl or 4-methoxyphenylmethyl, in which any functional group may be protected, any amino group may be acylated and any carboxyl group present may be amidated; or a group —[Alk]$_n$R$_7$ where Alk is a ($C_1$–$C_6$)alkyl or ($C_2$–$C_6$)alkenyl group optionally interrupted by one or more —O—, or —S— atoms or —N(R$_{12}$)— groups [where $R_{12}$ is a hydrogen atom or a ($C_1$–$C_6$)alkyl group], n is 0 or 1, and $R_7$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ hydrogen and $R_a$ and $R_b$ are independently phenyl or heteroaryl such as pyridyl; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, (C$_1$–C$_4$)perfluoroalkyl, —CH$_2$OH, —CO$_2$ (C$_1$–C$_6$)alkyl, —O(C$_1$–C$_6$)alkyl, —O(C$_2$–C$_6$)alkenyl, —S(C$_1$–C$_6$)alkyl, —SO(C$_1$–C$_6$)alkyl, —SO$_2$(C$_1$–C$_6$) alkyl, —S(C$_2$–C$_6$)alkenyl, —SO(C$_2$–C$_6$)alkenyl, —SO$_2$(C$_2$–C$_6$)alkenyl or a group —Q—W wherein Q represents a bond or —O—, —S—, —SO— or —SO$_2$— and W represents a phenyl, phenylalkyl, (C$_3$–C$_8$)cycloalkyl, (C$_3$–C$_8$)cycloalkylalkyl, (C$_4$–C$_8$) cycloalkenyl, (C$_4$–C$_8$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$–C$_6$)alkyl, —CONH$_2$, —CONH (C$_1$–C$_6$)alkyl, —CONH(C$_1$–C$_6$alkyl)$_2$, —CHO, —CH$_2$OH, (C$_1$–C$_4$)perfluoroalkyl, —O(C$_1$–C$_6$)alkyl, —S(C$_1$–C$_6$)alkyl, —SO(C$_1$–C$_6$)alkyl, —SO$_2$(C$_1$–C$_6$) alkyl, —NO$_2$, —NH$_2$, —NH(C$_1$–C$_6$)alkyl, —N((C$_1$–C$_6$)alkyl)$_2$, —NHCO(C$_1$–C$_6$)alkyl, (C$_1$–C$_6$) alkyl, (C$_2$–C$_6$)alkenyl, (C$_2$–C$_6$)alkynyl, (C$_3$–C$_8$) cycloalkyl, (C$_4$–C$_8$)cycloalkenyl, phenyl or benzyl.

Examples of particular $R_3$ groups include benzyl, phenyl, cyclohexylmethyl, pyridin-3-ylmethyl, tert-butoxymethyl, n-propyl, iso-propyl, iso-butyl, sec-butyl, tert-butyl, 1-benzylthio-1-methylethyl, 1-methylthio-1-methylethyl, and 1-mercapto-1-methylethyl. Presently preferred $R_3$ groups include methyl benzyl, tert-butyl, iso-butyl, phenyl and iso-propyl.

Examples of particular ester and thioester groups $R_4$ groups include those of formula —(C=O)OR$_9$, —(C=O)SR$_9$, —(C=S)SR$_9$, and —(C=S)OR$_9$ wherein R$_9$ is (C$_1$–C$_6$)alkyl, (C$_2$–C$_6$)alkenyl, cycloalkyl, cycloalkyl(C$_1$–C$_6$)alkyl-, phenyl, heterocyclyl, phenyl(C$_1$–C$_6$)alkyl-, heterocyclyl(C$_1$–C$_6$)alkyl-, (C$_1$–C$_6$)alkoxy(C$_1$–C$_6$)alkyl-, (C$_1$–C$_6$)alkoxy(C$_1$–C$_6$)alkoxy(C$_1$–C$_6$)alkyl-, any of which may be substituted on a ring or non-ring carbon atom or on a ring heteroatom, if present. Examples of such R$_9$ groups include methyl, ethyl, n-and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methylcyclopent-1-yl, adamantyl, tetrahydrofuran-3-yl and methoxyethyl.

Presently preferred are compounds of formula (IB) wherein $R_4$ is a carboxylate ester of formula —(C=O)OR$_9$, wherein R$_9$ is benzyl, cyclopentyl, isopropyl or tert-butyl.

Specific examples of compounds useful as antibacterial agents in accordance with the invention include those of the preparative examples herein, and pharmaceutically or veterinarily acceptable salts thereof.

Compounds of formula (I) may be prepared by causing an acid of formula (II) or an activated derivative thereof to react with an amine of formula (III)

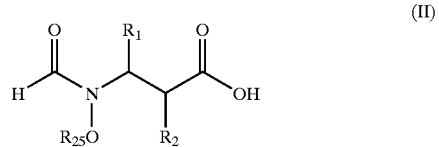
(II)

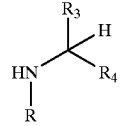
(III)

wherein $R_1$, $R_2$, $R_3$ and $R_4$ are as defined in general formula (I) except that any substituents in $R_1$, $R_2$, $R_3$ and $R_4$ which are potentially reactive in the coupling reaction may themselves be protected from such reaction, and $R_{25}$ is as defined in relation to formula (I) above, and optionally removing protecting groups from $R_1$, $R_2$, $R_3$ and $R_4$.

Compounds of formula (II) may be prepared by N-formylation, for example using acetic anhydride and formic acid, of compounds of formula (IV)

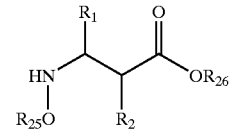
(IV)

wherein $R_1$, $R_2$ and $R_{25}$ are as defined in relation to formula (I) and $R_{26}$ is a hydroxy protecting group, and thereafter removing the protecting group $R_{26}$.

A compound of general formula (IV) may be prepared by reduction of an oxime of general formula (V)

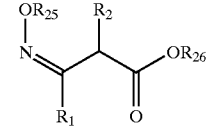
(V)

wherein $R_1$, $R_2$, $R_{25}$ and $R_{26}$ are as defined above. Reducing agents include metal hydrides (eg sodium cyanoborohydride in acetic acid, triethylsilane or boranelpyridine) and hydrogenation.

A compound of general formula (V) can be prepared by reaction of a β-keto carbonyl compound of general formula (VI)

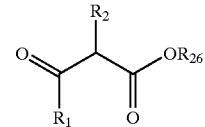
(VI)

wherein $R_1$, $R_2$, and $R_{26}$ are as defined above, with an O-protected hydroxylamine. β-keto carbonyl compounds (VI) may be prepared by acylation of the enolate derived from a carbonyl compound of formula (VII) or (VIIA)

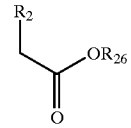
(VII)

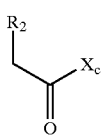
(VIIA)

wherein $R_2$ and $R_{26}$ are as defined above, and $X_c$ is a chiral auxiliary, with a compound of formula (VII)

(VII)

wherein $R_1$ is as defined above and Z is a leaving group such as chloro or alkoxy. Chiral enolates of type (VIIA) have been described by Evans (J. Am. Chem. Soc., 104, 1737, (1982)).

Another method for the preparation of a compound of general formula (IV) is by Michael addition of a hydroxylamine derivative to an α, β-unsaturated carbonyl compounds of general formula (IX)

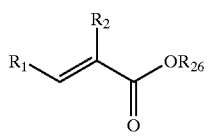
(IX)

wherein $R_1$, $R_2$, and $R_{26}$ are as defined above. The α,β-unsaturated carbonyl compounds (IX) may be prepared by standard methods.

Further details of the synthetic routes to compounds for use in accordance with the invention appear in the preparative examples herein.

Salts of the compounds for use in accordance with the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

In the hospital setting to combat severe bacterial infections, the active ingredient may be administered by intravenous infusion.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Although it may be of interest to establish the mechanism of action of the compounds used in the present invention, it is their ability to inhibit bacterial growth per se which is of practical significance. Without wishing to be bound by any specific mode of action or mechanism by which the compounds operate, it is presently believed that the antibacterial activity of the compounds with which the invention is concerned may be due, at least in part, to inhibition of bacterial polypeptide deformylase (PDF) enzyme.

Bacterial polypeptide deformylase (PDF)(for example EC 3.5.1.31) is a family of metalloenzymes which is essential for bacterial viability, its function being to remove the formyl group from the N-terminal methionine residue of ribosome-synthesised proteins in eubacteria. Mazel et al. (EMBO J. 13(4):914–923, 1994) have recently cloned and characterised a PDF. As PDF is is essential to the growth of bacteria and there is no eukaryotic counterpart to PDF, Mazel et al. (ibid), Rajagopalan et al. (J. Am. Chem. Soc. 119:12418–12419, 1997) and Becker et al., (J. Biol Chem. 273(19):11413–11416, 1998) have each proposed that PDF is an excellent anti-bacterial target.

The following preparative examples describe the synthesis of compounds having antibacterial activity, in accordance with the invention.

$^1$H and $^{13}$C NMR spectra were recorded using a Bruker DPX 250 spectrometer at 250.1 and 62.9 MHz, respectively. Mass spectra were obtained using a Perkin Elmer Sciex API 165 spectrometer using both positive and negative ionisation modes. Infra-red spectra were recorded on a Perkin Elmer PE 1600 FTIR spectrometer.

Analytical HPLC was performed on a Beckman System Gold, using Waters Nova Pak C18 column (150 mm, 3.9 mm) with 20 to 90% solvent B gradient (1 ml/min) as the mobile phase. [Solvent A: 0.05% TFA in 10% water 90% methanol; Solvent B: 0.05% TFA in 10% methanol 90%/], detection wavelength at 230 nm. Preparative HPLC was performed on a Gilson autoprep instrument using a C18 Waters delta prep-pak cartridge (15 μm, 300 A, 25 mm, 10 mm) with 20 to 90% solvent B gradient (6 ml/min) as the mobile phase. [Solvent A water; Solvent B: methanol], UV detection was at 230 nm.

The following abbreviations have been used in the examples:

DMF—N,N-Dimethylformamide
HOBT—1-Hydroxybenzotriazole
EDC—N-(3-Dimethylaminopropyl)N'-ethylcarbodiimide hydrochloride
HCl—Hydrochloric acid
THF—Tetrahydrofuran

EXAMPLE 1

2S-[2-(R,S)-Benzyl-3-(formyl-hydroxy-amino)-propionylamino]-3-phenyl-propionic acid cyclopentyl ester

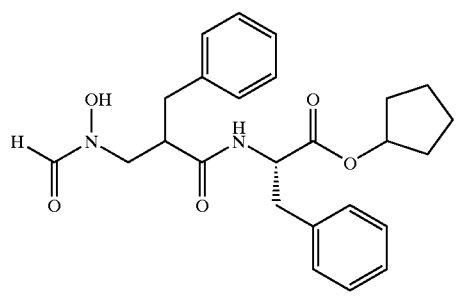

Example 1 was prepared as outlined in Scheme 1 using procedures described below.

Scheme 1

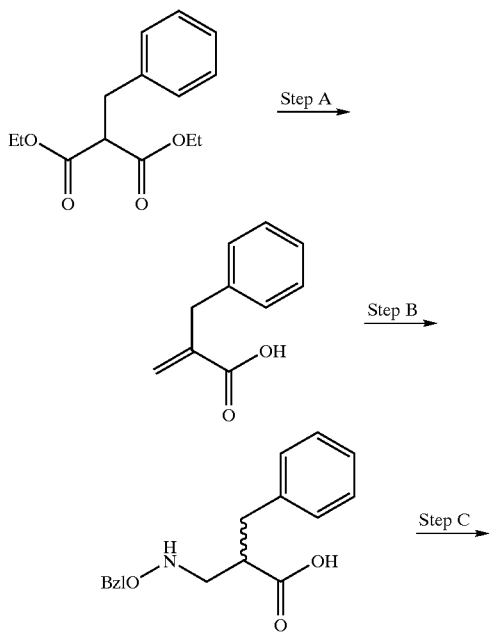

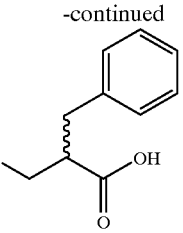

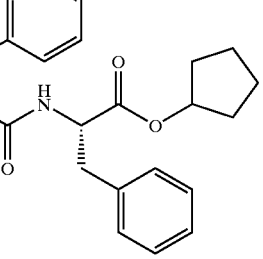

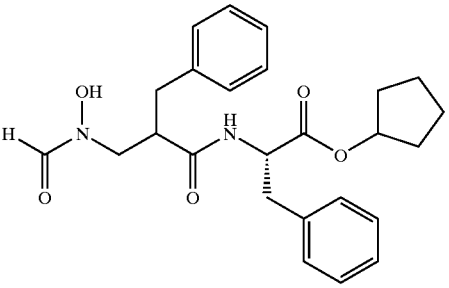

Reagents and conditions: A. (1) EtOH/KOH/H₂O, reflux 5 hours, (2) piperidine, HCHO, EtOH, reflux 4 hours; B. H₂NOBzl, 80° C. o/n; C. HCOOH, Ac₂O; D. WSCDI, HOBT, DMF, L-phenylalanine cyclopentyl ester r.t., 18 hours; E. H₂(g), Pd catalyst, EtOH 90 minutes.

(a) 2-Benzyl-acrylic Acid

Diethyl benzylmalonate (100 g, 400 mmol) was dissolved in ethanol (300 mL) and treated with a solution of potassium hydroxide (134.4 g, 2.4 mol) in water (500 mL). The mixture was heated under reflux for 5 hours and then allowed to cool. Ethanol was removed under reduced pressure and the remaining aqueous solution cooled in ice and acidified to pH1 with concentrated HCl. The product was extracted with ethyl acetate (3×200 mL). The combined extracts were washed with brine, dried over magnesium sulphate, filtered and concentrated under reduced pressure to yield benzyl-malonic acid as a white crystalline solid. The solid was taken-up in ethanol (250 mL) and treated portionwise with piperidine (33 g, 397 mmol) followed by an aqueous solution of formaldehyde (37%, 150 mL) which resulted in formation of a white precipitate. The reaction mixture was heated and treated with methanol (50 mL) to give a homogeneous solution. Following dissolution the reaction mixture was heated under reflux for 4 hours. The reaction mixture was concentrated under reduced pressure. The aqueous residue was acidified to pH1 with 1 M HCl and the product extracted with ethyl acetate (3×150 mL). The combined extracts were washed with brine, dried over magnesium sulphate, filtered and concentrated under reduced pressure to yield 2-benzyl-acrylic acid as a colourless oil which crystallized on standing (45 g, 75%). $^1$H-NMR; δ (CDCl₃), 7.32–7.17 (5H, m), 6.36 (1H, s), 5.54 (1H, d, J=1.3 Hz), 3.61 (2H, s).

(b) 2-(R,S)-Benzyl-3-benzyloxyamino-propionic Acid

A mixture of 2-benzyl-acrylic acid (8.0 g, 55 mmol) and O-benzylhydroxylamine (16.0 g, 130 mmol) was heated at 80° C. for 18 hours. The reaction mixture was cooled, diluted with diethyl ether (100 mL) and extracted with 1M sodium carbonate (3×100 mL). The combined aqueous extracts were acidified with 3M citric acid and then re-extracted with dichloromethane (3×100 mL). The combined organic extracts were washed with brine, dried over magnesium sulphate, filtered and concentrated under reduced pressure to yield 2-(R,S)-benzyl-3-benzyloxyamino-propionic acid as a white crystalline solid (7.82 g, 53%). $^1$H-NMR; δ (CDCl$_3$), 7.61–7.15 (10H, m), 4.66 (2H, d, J=1.7 Hz), 3.13–2.94 (4H, m), 2.84–2.74 (1H, m).

(c) 2-(R,S)-Benzyl-3-(benzyloxy-formyl-amino)-propionic Acid

A solution of 2-(R,S)-benzyl-3-benzyloxyamino-propionic acid (7.8 g, 27.4 mmol) in formic acid (40 mL) was cooled in an ice-water bath and treated dropwise with acetic anhydride (15 mL). The reaction was allowed to warm to room temperature and stirred for 18 hours. The reaction mixture was diluted with dichloromethane (150 mL) and partitioned with water (100 mL). The organic layer was separated, washed with brine, dried over magnesium sulphate, filtered and concentrated under reduced pressure to yield 2-(R,S)-benzyl-3-(benzyloxy-formyl-amino)-propionic acid as a colourless oil (7.8 g, 91%). $^1$H-NMR; δ (CDCl$_3$), 7.87–7.16 (10H, m), 4.92–4.66 (2H, m), 4.03–3.90 (2H, m), 3.17–2.93 (2H, m), 2.78–2.70 (1H, m).

(d) 2S-[2-(R,S)-Benzyl-3-(benzyloxy-formyl-amino)-propionylamino]-3-phenyl Propionic Acid Cyclopentyl Ester 2-(R,S)-Benzyl-3-(benzyloxy-formyl-amino)-propionic acid (2.89 g, 9.3 mmol) was dissolved in DMF (20 mL) and treated with HOBT (1.35 g, 10 mmol) and EDC (1.91 g, 10 mmol). The reaction mixture was stirred at room temperature for 1 hour before the addition of a solution of L-phenylalanine cyclopentyl ester (2.4 g, 10.3 mmol) in DMF (10 mL). The reaction mixture was stirred at room temperature for 18 hours. DMF was removed under reduced pressure and the residue partitioned between ethyl acetate and 1M HCl. The organic layer was separated and washed with 1M HCl, saturated aqueous sodium bicarbonate solution and brine before drying over magnesium sulphate, filtration and concentration under reduced pressure to yield 2S-[2-(R,S)benzyl-3-(benzyloxy-formyl-amino)-propionylamino]-3-phenylpropionic acid cyclopentyl ester (3.6 g used crude in step e).

(e) 2S-[2-(R,S)-Benzyl-3-(formyl-hydroxy-amino)-propionylamino]-3-phenyl-propionic Acid Cyclopentyl Ester A solution of 2S-[2-(R,S)-benzyl-3-(benzyoxy-formyl-amino)-propionylamino]-3-phenyl propionic acid cyclopentyl ester (3.6 g crude from step d) in ethanol (30 mL) was treated with a palladium catalyst (100 mg, 10%Pd on charcoal). The reaction mixture was stirred under an atmosphere of hydrogen gas for 90 minutes. Catalyst was removed by filtration and the filtrate concentrated to a colourless oil. Using reverse phase chromatography 200 mg of the crude product was fractionated to provide two diastereoisomers of 2S-[2-benzyl-3-(formyl-hydroxy-amino)-propionylamino]-3-phenyl-propionic acid cyclopentyl ester. Diastereoisomer A (35 mg), $^1$H-NMR; δ (CDCl$_3$), 8.34 and 7.77 (1H, 2xs), 7.29–6.84 (10H, m), 6.13 (1H, d, J=7.3 Hz), 5.11–5.00 (1H, m), 4.67–4.49 (1H, m), 3.99–3.79 (1H, m), 3.66–3.60 and 3.51–3.47 (1H, 2xm), 3.05–2.69 (5H, m) and 1.85–1.45 (8H, m); $^{13}$C-NMR; δ 174.4, 172.3, 171.4, 171.2, 138.2, 136.3, 129.8, 129.6, 129.2, 128.9, 127.5, 127.4, 127.2, 79.4, 78.9, 54.3, 54.0, 51.9, 51.1, 48.8, 47.9, 46.6, 38.7, 38.1, 36.8, 36.5, 33.0, 32.8 and 24.0. Diastereoisomer B (42 mg), $^1$H-NMR; δ (CDCl$_3$), 8.35 and 7.71 (1H , 2xs), 7.33–7.15 (8H, m), 7.08–6.94 (1H, bm), 6.83–6.73 (2H, m), 6.20 and 5.94 (2xd), 5.30–5.08 (1H, m), 4.73–4.64 (1H, m), 3.85–3.76 (1H, m), 3.56–3.47 (1H, m), 3.01–2.68 (5H, m) and 1.91–1.45 (8H, m); $^{13}$C-NMR; δ (CDCl$_3$), 174.2, 172.9, 172.4, 171.8, 138.7, 136.1, 129.6, 129.3, 129.1, 128.9, 128.8, 127.6, 127.5,127.4, 127.3, 127.2, 127.1, 79.9, 79.2, 53.9, 53.6, 52.3, 50.3, 48.1, 47.0, 38.3, 37.5, 36.9, 36.4, 32.9, 32.8 and 24.0.

EXAMPLE 2

2S-{2R-[1-(R,S)-(Formyl-hydroxy-amino)-ethyl]-4-methyl-pentanoylamino}-3-phenylpropionic Acid Cyclopentyl Ester

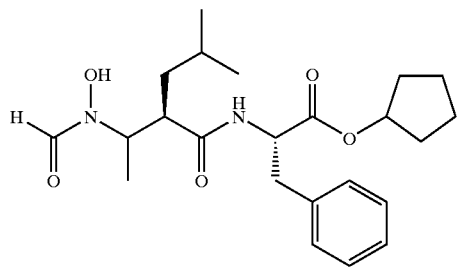

Example 2 was prepared as outlined in scheme 2 using procedures described below.

Scheme 2

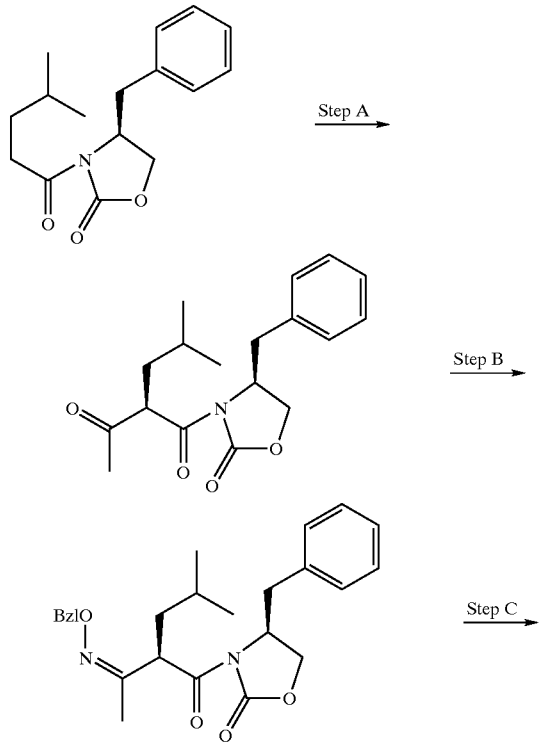

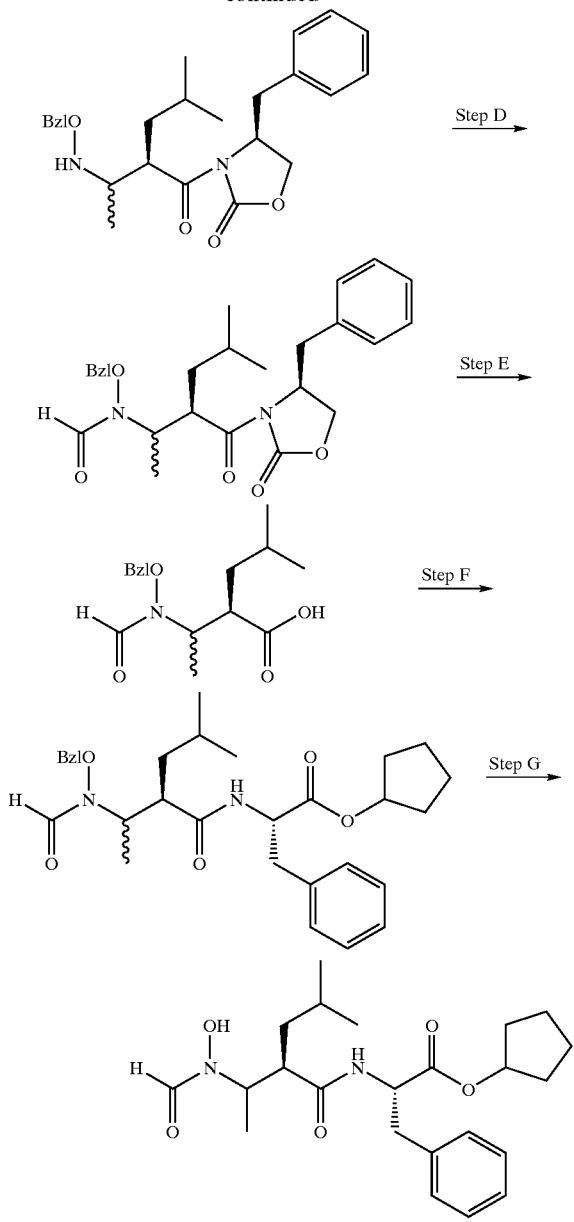

Reagents and conditions: A. Sodium hexamethyldisilazide, AcCl, −60° C. 3 hours; B. BzlONH₂HCl, NaOAc, H₂O/EtOH, 50° C. 18 hours; C. AcOH, NaCNBH₃, 25 hours; D. HCOOH, AcOH, 18 hours; E. LiOH, H₂O₂, THF/H₂O, 4 hours; F. L-Phenylalanine cyclopentyl ester, HOBT, WSCDI, DMF, 48 hours; G. H₂(g), Pd catalyst, EtOH, 2 hours.

(a) 1-(4S-Benzyl-2-oxo-oxazolidin-3-yl)-2R-isobutyl-butane-1,3-dione

A solution of 4S-benzyl-3-(4-methyl-pentanoyl)-oxazolidin-2-one (31 g, 113 mmol) in anhydrous THF (750 mL) was cooled to −70° C. under an inert atmosphere. Sodium hexamethyldisilazide (118 mL of a 1M solution, 118 mmol) was added via cannula whilst maintaining the temperature below −68° C. The reaction mixture was stirred at −70° C. for 30 minutes before the addition of acetyl chloride (10.2 mL, 135 mmol), again maintaining the temperature below −68° C. The reaction was slowly warmed to −60° C. and maintained at this temperature for 3 hours before quenching with acetic acid (6.75 g, 118 mmol) in diethyl ether (10 mL). The solvent was removed under reduced pressure and the resulting slurry taken up in ethyl acetate and washed with brine. The organic layer was dried over sodium sulphate, filtered and concentrated under reduced pressure to leave an oil (36 g) which was shown by NMR to contain the title compound contaminated with 15% of the starting material. ¹H-NMR; δ (CDCl₃), 7.3–7.22 (5H, m), 4.69–4.65 (1H, m), 4.63–4.57 (1H, dd, J=3.2 Hz), 4.22–4.13 (2H, m), 3.41 (1H, dd, J=3.2 Hz), 2.74 (1H, dd, J=9.8 Hz), 2.31 (3H, s), 2.10–2.04 (1H, m), 1.68–1.60 (1H, m), 1.49–1.39 (1H, m) and 0.97 (6H, 2xd, J=6.5 Hz).

(b) 1-(4S-Benzyl-2-oxo-oxazolidin-3-yl)-2R-isobutyl-butane 1,3-dione 3-(O-benzyl-oxime)

1-(4S-Benzyl-2-oxo-oxazolidin-3-yl)-2R-isobutyl-butane-1,3-dione (35.5 g, 112 mmol) was dissolved in waterlethanol (500 mL, 10% vol/vol) and treated with benzylhydroxylamine hydrochloride (21.4 g, 134 mmol) and sodium acetate (18.3 g, 134 mmol). The reaction mixture was stirred at 50° C. for 18 hours. The solution was concentrated under reduced pressure to give a white precipitate of the product which was collected by filtration (21.0 g, 44%). ¹H-NMR; δ (CDCl₃), 7.38–7.08 (10H, m), 5.15–5.04 (2H, m), 4.574.47 (1H, m), 4.24 (1H, dd, J=3.6 Hz), 4.07 (1H, dd, J=8.9 Hz), 3.92 (1H, dd, J=2.6 Hz), 3.16 (1H, dd, J=2.7 Hz), 2.09 (3H, s), 2.04–1.98 (1H, m), 1.76–1.66 (1H, dd, J=11.0 Hz), 1.63–1.60 (1H, m), 1.45–1.35 (1H, m) and 0.94 (6H, 2xd, J=6.6 Hz).

(c) 4S-Benzyl-3-[2R-(1-(R,S)-benzyloxyamino-ethyl)-4-methyl-pentanoyl]-oxazolidin-2-one 1-(4S-Benzyl-2-oxo-oxazolidin-3-yl)-2R-isobutyl-butane 1,3-dione 3-(O-benzyl-oxime) (21 g, 50 mmol) was dissolved in acetic acid (400 mL) and sodium cyanoborohydride (6.24 g, 100 mmol) added portionwise. The mixture was stirred for 18 hours at room temperature then a further equivalent of sodium cyanoborohydride added. Stirring was continued for a further 7 hours then the reaction mixture concentrated under reduced pressure. The resultant oil was taken up in dichloromethane (600 mL) then carefully washed with sodium carbonate and brine. The organic layer was dried over magnesium sulphate, filtered and evaporated to a colourless oil (21 g). Column chromatography on silica gel using DICHLOROMETHANE as eluent lead to isolation of the desired product as a mixture of diastereoisomers (9.05 g, 43%). ¹H-NMR; δ (CDCl₃), 7.37–7.18 (10H, m), 5.80 (1H, bs), 4.70–4.60 (3H, m), 4.13 (1H, m), 4.12–4.05 (2H, m), 3.91 (1H, m), 3.43–3.36 (1H, m), 2.48–2.37 (1H, m), 2.00–1.75 (1H, m), 1.70–1.64 (1H, m), 1.40–1.31 (1H, m), 1.24 (3H, m) and 0.94–0.87 (6H, m).

(d) N-[2-(4S-Benzyl-2-oxo-oxazolidine-3S-carbonyl)-1-(R,S), 4-dimethyl-pentyl]-N-benzyloxyformamide 4S-Benzyl-3-[2R-(1-(R,S)-benzyloxyamino-ethyl)-4-methyl-pentanoyl]-oxazolidin-2-one (12.7 g, 30 mmol) was taken up in formic acid (250 mL) and stirred at 0° C. while acetic anhydride (50 mL) was added dropwise. The mixture was stirred at room temperature for 18 hours. The reaction mixture was concentrated under reduced pressure, taken up in DICHLOROMETHANE and washed with saturated sodium bicarbonate and brine. The solution was dried over magnesium sulphate, filtered and concentrated to yield the title compound as a colourless oil (12.7 g, 94%). ¹H-NMR; δ (CDCl₃, mixture of diastereoisomers), 8.35 and 8.14 (1H, 2xbs), 7.55–7.15 (10H, m), 5.20–4.90 (2H, bm), 4.73–4.46 (2H, m), 4.20–4.01 (3H, m), 3.31 (1H, dt, J=13.2, 3.2 Hz), 2.51–2.30 (1H, m), 1.95–1.74 (1H, bm), 1.54–1.33 (5H, bm), 0.98–0.85 (6H, m).

(e) 2R-[1-(R,S)-(Benzyloxy-formyl-amino)-ethyl]-4-methyl-pentanoic Acid

N-[2-(4S-Benzyl-2-oxo-oxazolidine-3S-carbonyl)-1-(R,S), 4-dimethyl-pentyl]-N-benzyloxyformamide (7.30 g, 16.1 mmol) was dissolved in THF (210 mL) and water (60 mL) and cooled to 0° C. Hydrogen peroxide (1.84 mL, 30% solution, 64.5 mmol) was added dropwise followed by aqueous lithium hydroxide (1.02 g in 10 mL, 24.2 mmol) and the solution stirred at 0° C. for 4 hours. The reaction mixture was quenched by the addition of sodium nitrite (1.11 g, 16 mmol). THF was removed under reduced pressure and the chiral auxilliary removed by extraction into dichloromethane. The aqueous solution was was neutralised (pH5) with 1M HCl and extracted with ethyl acetate. The combined extracts were dried over magnesium sulphate, filtered and concentrated to yield the product as a yellow oil (3.78 g, 80%). $^1$H-NMR; δ (CDCl$_3$, mixture of diastereoisomers), 8.40 and 8.00 (1H, 2xs), 7.52–7.26 (5H, m), 5.25–4.85 (2H, 2xbd), 4.45 (1H, m), 3.85 (1H, bm), 2.90 (1H, bm), 1.75–1.48 (2H, bm), 1.48–1.20 (4H, bm) and 1.00–0.84 (6H, m).

(f) 2S-{2R-[1-(R,S)-(Benzyloxy-formyl-amino)-ethyl]-4-methyl-pentanoylamino}-3-phenyl-propionic Acid Cyclopentyl Ester A solution of 2R-[1-(R,S)-(benzyloxy-formyl-amino)-ethyl]-4-methyl-pentanoic acid (410 mg, 1.40 mmol) in DMF (10 mL) was treated with HOBt (227 mg, 1.68 mmol) and EDC (322 mg, 1.68 mmol). A solution of L-phenylalanine cyclopentyl ester (394 mg, 1.68 mmol) in DMF (2 mL) was added to the reaction mixture. The reaction was stirred at room temperature for 48 hours. DMF was removed by evaporation under reduced pressure. The residue was taken up in ethyl acetate and washed with 1M HCl, saturated sodium bicarbonate and brine, before drying over magnesium sulphate, filtration and concentration to a colourless oil. The product was purified by column chromatography on silica gel eluting with 20–40% ethyl acetate/hexane. Product containing fractions were combined and solvent evaporated to provide the title compound as an off-white foam (571 mg, 66%). $^1$H-NMR; δ (CDCl$_3$, mixture of diastereoisomers), 8.19 and 7.97 (1H, 2xs), 7.50–6.90 (10H, m), 6.09 and 5.94 (1H, 2xbd), 5.34–5.02 (2H, m), 4.95 4.74 (2H, m), 3.91–3.61 (2H, 2xbm), 3.15–2.80 (2H, m), 2.80–2.60 and 2.55–2.35 (1H, 2xm), 1.92–1.35 (11H, m), 1.22–1.00 (2H, m), 0.95–0.82 (6H, m).

(g) 2S-{2R-[1-(R,S)-(Formyl-hydroxy-amino)-ethyl]-4-methyl-pentanoylamino}-3-phenylpropionic Acid Cyclopentyl Ester A solution of 2S-{2R-[1-(R,S)-(benzyloxy-formyl-amino)-ethyl]-4-methyl-pentanoyl amino}-3-phenyl-propionic acid cyclopentyl ester (447 mg, 0.88 mmol) in ethanol (25 mL) was treated with palladium catalyst (89 mg, 10% Pd on charcoal) as a slurry in ethyl acetate (2 mL). Hydrogen gas was bubbled through the resulting suspension for 2 hours. The catalyst was removed by filtration and the filtrate concentrated under reduced pressure to a white foam. The reaction product was separated by preparative reverse phase chromatography to yield two diastereoisomers. Diastereoisomer A (41 mg, 11%), $^1$H-NMR; δ (methanol-d$_4$), 8.60 (0.6H, d, J=8.2 Hz), 8.52 (0.4H, d, J=8.2 Hz), 8.24 (0.4H, s), 7.90 (0.6H, s), 7.84–7.15 (5H, m), 5.15 (1H, m), 4.79–4.71 (1H, m), 4.34–4.22 (0.4H, m), 3.66–3.54 (0.7H, m), 3.25–3.15 (1H, m), 2.90 (1H, dd, J=14.0, 10.4 Hz), 2.70–2.56 (1H, m), 1.87–1.40 (10H, bm), 1.13–0.97 (1H, m) and 0.91–0.75 (9H, bm); $^{13}$C-NMR; δ (methanol-d$_4$), 175.9, 172.8, 138.4, 130.2, 129.5, 127.9, 59.0, 55.2, 55.1, 54.2, 48.8, 40.4, 40.2, 38.3, 33.5, 26.6, 26.5, 24.7, 24.6, 21.7, 17.1 and 16.0. Diastereoisomer B (28 mg, 8%), $^1$H-NMR; δ (methanol-d$_4$), 7.95 (0.4H, s), 7.84 (0.6H, s), 7.26–7.21 (5H, m), 5.13 (0.4H, m), 5.04 (0.6H, m), 4.73–4.66 (0.4H, m), 4.62–4.56 (0.6H, m), 4.42–4.36 (0.4H, m), 3.89–3.78 (0.6H, m), 3.18–2.61 (3H, bm), 1.77–1.44 (10H, m), 1.29–1.11 (3H, m), 1.00–0.87 (7H, m); $^{13}$C-NMR; δ (methanol-d$_4$), 172.7, 138.0, 130.4, 129.5, 127.9, 79.6, 59.0, 53.3, 49.6, 39.9, 38.8, 38.4, 33.5, 33.4, 27.1, 26.7, 24.7, 24.6, 24.3, 24.1, 22.1, 21.9, 16.2 and 15.2.

EXAMPLE 3

2S{-2R-[(Formyl-hydroxy-amino)-methyl]-hexanoylamino}-3,3-dimethyl Butyric Acid Cyclopentyl Ester

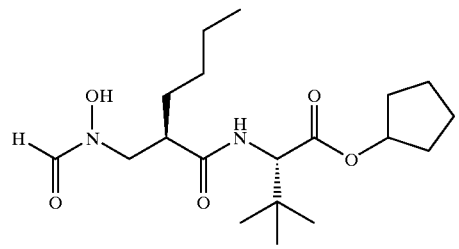

Thehe title compound was prepared as outlined in Scheme 3 and is described in detail below:

Scheme 3

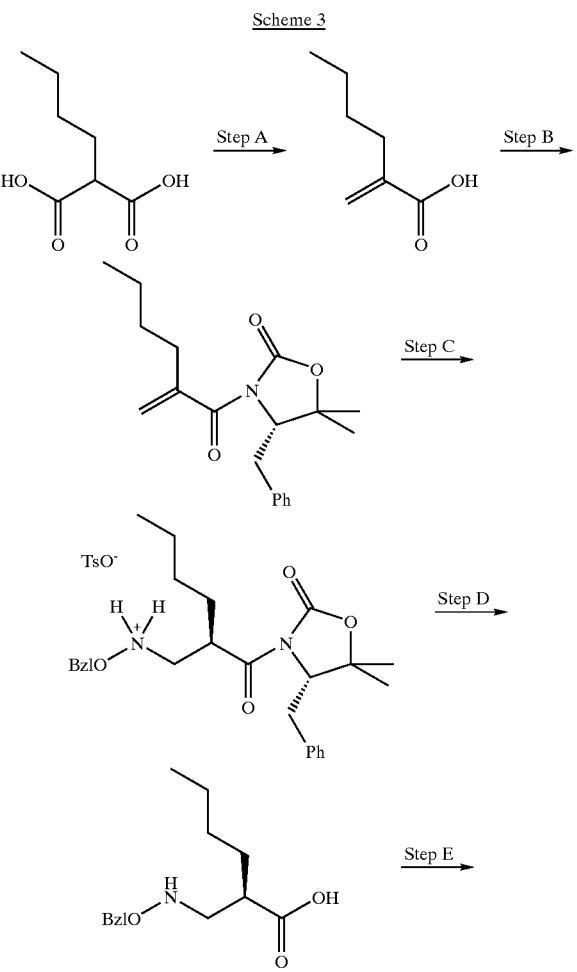

-continued

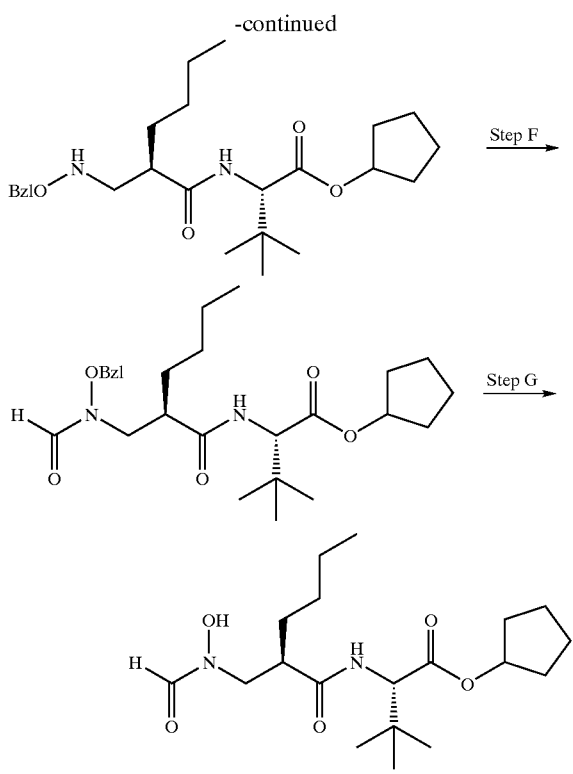

Reagents amd conditions: A. piperidine, HCHO, EtOH, 80° C., o/n;
B. ᵗBuCOCl, Et₃N then 3-lithio-4-benzyl-5,5-dimethyl-oxazolidin-2-one; C. H₂NOBzl, room temp., o/n then pTsOH, EtOAc; D. LiOH, aq THF, 0° C.; E. H-t-Leu-OcPentyl, HOBT, EDC, DMF;
F. HCOBt, THF; G. H₂, Pd/C. EtOH.

Step A: 2-Butyl Acrylic Acid

To a solution of n-butylmalonic acid (17.2 g, 107 mmol) in ethanol (200 ml) was added piperidine (12.76 ml, 129 mmol) and 37% aq. formaldehyde (40.3 ml, 538 mmol). The solution was heated to 80° C. during which time a precipitate appeared and then gradually redissolved over 1 hour. The reaction mixture was stirred at 80° C. overnight then cooled to room temperature. The solvents were removed under reduced pressure and the residue was dissolved in ethyl acetate (200 ml), washed successively with 1M hydrochloric acid and brine, dried over anhydrous magnesium sulfate and filtered. The filtrate was concentrated to give the title compound as a clear oil (13.37 g, 97%). ¹H-NMR; δ (CDCl₃), 6.29 (1H, s), 5.65 (1H, s), 2.34–2.28 (2H, m), 1.54–1.26 (4H, m) and 0.94 (3H, t, J=7.1 Hz).

Step B: 4S-Benzyl-3-(2-butyl-acryloyl)-5,5-dimethyl-oxazolidin-2-one

2-Butyl acrylic acid (21.5 g, 168 mmol) was dissolved in dry THF (500 ml) and cooled to −78° C. under a blanket of argon. Triethylamine (30 ml, 218 mmol) and pivaloyl chloride (21 ml, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissolved in dry THF (500 ml) and cooled to −78° C. under a blanket of argon. n-Butyllithium (2.4M solution in hexanes, 83 ml, 200 mmol) was added slowly and the mixture was stirred for 30 minutes at room temperature. The resulting anion was transferred via a cannula into the original reaction vessel. The mixture was allowed to warm to room temperature and stirred overnight at room temperature. The reaction was quenched with 1M potassium hydrogen carbonate (200 ml) and the solvents were removed under reduced pressure. The residue was partitioned between ethyl acetate and water. The organic layer was washed with brine, dried over anhydrous magnesium sulphate, filtered and concentrated under reduced pressure to an orange oil. TLC analysis revealed the presence of unreacted chiral auxiliary in addition to the required product. A portion of the material (30 g) was dissolved in dichloromethane and flushed though a silica pad to give pure title compound as a yellow oil (25.3 g). ¹H-NMR; δ (CDCl₃), 7.31–7.19 (5H, m), 5.41 (2H,s), 4.51 (1H, dd, J=9.7, 4.2 Hz), 3.32 (1H, dd, J=14.2, 4.2 Hz), 2.82 (1H, dd, J=14.2, 9.7 Hz), 2.40–2.34 (2H, m), 1.48–1.32 (4H, m), 1.43 (3H, s), 1.27 (3H, s) and 0.91 (3H, t, J=7.1 Hz). Some chiral auxiliary was recovered by flushing the silica pad with methanol.

Step C: 4S-Benzyl-3-[2-(benzyloxyamino-methyl)-hexanoyl]-5,5-dimethyl-oxazolidin-2-one (p-toluenesulfonic Acid Salt)

4S-Benzyl-3-(2-butyl-acryloyl)-5,5-dimethyl-oxazolidin-2-one (19.8 g, 62.8 mmol) was mixed with O-benzylhydroxylamine (15.4 g, 126 mmol) and stirred overnight at room temperature. The mixture was dissolved in ethyl acetate and the solution was washed with 1M hydrochloric acid, 1M sodium carbonate and brine, dried over anhydrous magnesium sulfate and filtered. The filtrate was concentrated under reduced pressure to a pale yellow oil (25.3 g) which was shown by NMR and HPLC analysis to contain 4S-Benzyl-3-[2-(benzyloxyamino-methyl)-hexanoyl]-5,5-dimethyl-oxazolidin-2-one (ca. 82% d.e.) along with a trace of starting material. The product was combined with a another batch (26.9 g, 76% d.e.) and dissolved in ethyl acetate (200 ml). p-Toluenesulfonic acid (22.7 g, 119 mmol) was added and the mixture was cooled to 0° C. The title compound was obtained as a white crytalline solid by seeding and scratching. Yield: 25.2 g, (34%, single diastereoisomer). A second crop (14.7 g, 20%, single diastereoisomer) was also obtained. ¹H-NMR; δ (CDCl₃), 7.89 (2H, d, J=8.2 Hz), 7.37–7.12 (10H, m), 7.02 (2H, d, J=6.9 Hz), 5.28–5.19 (2H,m), 4.55 (1H, m), 4.23 (1H, m), 3.93 (1H, m), 3.58 (1H, m), 2.58 (1H, m), 2.35 (3H, s), 1.67–1.51 (2H, m), 1.29–1.16 (4H, m), 1.25 (3H, s), 1.11 (3H, s) and 0.80–0.75 (3H, m).

Step D: 2R-Benzyloxyamino-methyl)hexanoic Acid

4S-Benzyl-3-[2R-(benzyloxyamino-methyl)-hexanoyl]-5,5-dimethyl-oxazolidin-2-one p-toluenesulfonic acid salt (25.2 g, 40.2 mmol) was partitioned between ethyl acetate and 1M sodium carbonate. The organic phase was dried over anhydrous magnesium sulfate, filtered and evaporated under reduced pressure. The residual oil was dissolved in THF (150 ml) and water (50 ml) and cooled to 0° C. and treated with lithium hydroxide (1.86 g, 44.2 mmol). The solution was stirred for 30 minutes at 0° C., then overnight at room temperature. The reaction was acidified to pH4 with 1M citric acid and the solvents were removed. The residue was partitioned between dichloromethane and 1M sodium carbonate. The basic aqueous layer was acidified to pH4 with 1M citric acid and extracted three times with ethyl acetate. The combined organic layers were dried over anhydrous magnesium sulfate, filtered and concentrated to provide the title compound as a colourless oil (7.4 g, 73%). ¹H-NMR; δ (CDCl₃), 8.42 (2H, br s), 7.34–7.25 (5H, m), 4.76–4.66 (2H, m), 3.20–3.01 (2H, m), 2.73 (1H, m), 1.70–1.44 (2H, m), 1.34–1.22 (4H, m) and 0.92–0.86 (3H, m).

Step E: 2S-[2R-(Benzyloxyamino-methyl)hexanoylamino]-3,3-dimethyl Butyric Acid Cyclopentyl Ester 2R-Benzyloxyamino-methyl)-hexanoic acid (1.99 g, 7.93 mmol) was dissolved in DMF (50 ml) and the solution was cooled to 0°. EDC (874 mg, 4.56 mmol) and HOBt (62 mg, 0.46 mmol) were added and the mixture was stirred for 15 minutes. tert-Leucine cyclopentyl ester (1.0 g, 5.02 mmol) was added and the reaction was allowed to warm to room temperature and stirred overnight. The solvent was removed under reduced pressure and the residue was dissolved in ethyl acetate, washed successively with 1M hydrochloric acid, saturated sodium hydrogen carbonate and brine, dried and filtered. The solvent was removed to leave a yellow oil which was purified by flash chromatography (silica gel, 20% ethyl acetate in hexane) to afford the title compound (964 mg, 28%) $^1$H-NMR; δ (CDCl$_3$), 7.36–7.29 (5H, m) 6.62 (1H, br d, J=9.2 Hz), 5.69 (1H, br s), 5.22–5.18 (1H, m), 4.73 (2H, s), 4.42 (1H, d, J=9.4 Hz), 3.11–3.04 (2H,m), 2.51 (1H, m), 1.87–1.59 (10H, m), 1.30–1.23 (4H, m), 0.97 (9H, s) and 0.87 (3H, t, J=6.7 Hz).

Step F: 2S-{2R-[(Benzyloxy-formyl-amino)-methyl]-hexanoylamino}-3,3-dimethyl Butyric Acid Cyclopentyl Ester 2S-[2R-(Benzyloxyamino-methyl)-hexanoylamino]-3,3-dimethyl butyric acid cyclopentyl ester (947 mg, 2.19 mmol) was dissolved in dry THF (40 ml) and treated with 1-formyl-benzotriazole (354 mg, 2.41 mmol). The reaction was stirred overnight at room temperature. The solvent was removed under reduced pressure and the residue was dissolved in ethyl acetate and washed with 1M sodium carbonate solution and brine. The organic layer was dried over anhydrous magnesium sulfate, filtered and concentrated to dryness under reduced pressure. The desired product was obtained by flash chromatography (silica gel, eluting with 25% ethyl acetate in hexane). Yield: 814 mg (81%). $^1$H-NMR; δ (CDCl$_3$, rotamers), 8.13 (0.7H, br s), 7.88 (0.3H, br s), 7.37 (5H, br s), 6.02 (1H, br d, J=9.1 Hz), 5.18 (1H, m), 4.96 (1H, br s), 4.76 (1H, br s), 4.35 (1H, d, J=9.2 Hz), 3.74 (2H, br s), 2.53 (1H, m), 1.87–1.59 (10H, m), 1.28–1.23 (4H, m), 0.96–0.84 (3H, m) and 0.93 (9H, s).

Step G: 2S-{2R-[(Formyl-hydroxy-amino)-methyl]-hexanoylamino}-3,3-dimethyl Butyric Acid Cyclopentyl Ester 2S-{2R-[(Benzyloxy-formyl-amino)-methyl]-hexanoylamino}-3,3-dimethyl butyric acid cyclopentyl ester (780 mg, 1.69 mmol) was dissolved in ethanol (40 ml) and placed under a blanket of argon. 10% palladium on charcoal (80 mg) was added and the mixture was stirred vigorously as hydrogen gas was bubbled through the system. After 30 minutes the suspension was placed under a balloon of hydrogen and stirred overnight at room temperature. The flask was purged with argon before removing the catalyst by filtration. The filtrate was concentrated under reduced pressure to provide the title compound as a white foam (458 mg, 73%). $^1$H-NMR; δ (CD$_3$OD, rotamers), 0.84 (0.4H, s), 7.82 (0.6H, s), 5.19–5.15 (1H, m), 4.27 (1H, s), 3.82–3.61 (1.4H, m), 3.45–3.37 (0.6H, m), 3.10–2.88 (1H, m), 1.89–1.31 (14H, m), 1.01 (3.6H, s), 0.99 (5.4H, s) and 0.92–0.87 (3H, m). $^{13}$C-NMR; δ (CDCl$_3$ rotamers), 172.8, 171.1, 78.7, 78.4, 60.4, 60.2, 51.7, 48.0, 46.2, 44.8, 34.9, 34.7, 32.7, 32.6, 30.1, 29.9, 29.3, 29.2, 26.6, 23.6, 22.6 and 13.8. IR (refection disc) v$_{max}$ 2978, 1740, 1690, 1549, 1379, 1237, 1171, 984, 882 cm$^{-1}$. LRMS: 393 (M+Na), 369 (M−H).

The compounds of Examples 4–6 were preparedby the method of Example 3, by using the appropriate amino acid derivative instead of tert-leucine cyclopentyl ester in Step E:

EXAMPLE 4

2S-{2R-[(Formyl-hydroxy-amino)-methyl]-hexanoylamino}-3-phenyl-propionic Acid Cyclopentyl Ester

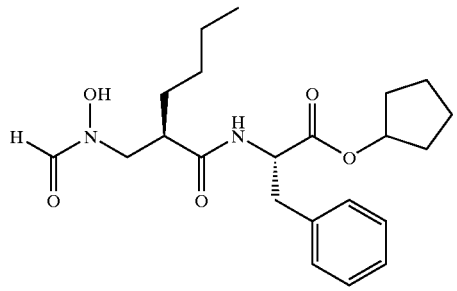

$^1$H-NMR; δ (CD$_3$OD rotamers), 8.13 (0.4H, s), 7.81 (0.6H, s), 7.36–6.92 (5H, m), 5.11–5.07 (1H, m), 4.61 (1H, t, J=7.6 Hz), 3.65–3.46 (1H, m), 3.42–3.30 (1H, m), 3.19–2.92 (2H, m), 2.89–2.77 (0.6H, m), 2.74–2.51 (0.4H, m), 1.98–1.29 (14H, m) and 0.89–0.81 (3H, m). $^{13}$C-NMR; δ (CD$_3$OD rotamers), 173.0, 171.6, 136.2, 129.8, 129.6, 129.1, 129.0, 127.7, 127.5, 79.6, 79.0, 53.9, 53.6, 51.9, 48.5, 46.4, 45.0, 38.6, 38.0, 33.0, 32.9, 30.3, 30.2, 29.6, 29.5, 24.0, 23.0 and 14.2. IR (reflection disc); v$_{max}$ 3325, 2958, 1731, 1663, 1532, 1443, 1367, 1280, 1199, 1104, 1079, 1032, 885, 749 and 699 cm$^{-1}$. LRMS; +ve ion 427 (M+Na); −ve ion 403 (M−1).

EXAMPLE 5

2S-{2R-[(Formyl-hydroxy-amino)methyl]-hexanoylamino}-3,3-dimethyl Butyric Acid Methyl Ester

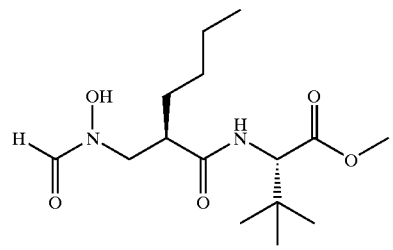

m.p. 63.5–64.5° C. $^1$H-NMR; δ (CD$_3$OD, rotamers), 8.24 (0.3H, s), 7.82 (0.7H, s), 4.33 (1H, s), 3.82–3.58 (1.3H, m), 3.70 (3H, s), 3.45–3.37 (0.7H, m), 3.11–3.01 (0.7H, m), 2.95–2.83 (0.3H, m), 1.55–1.20 (6H, m), 1.00 (3H, s), 0.99 (6H, s) and 0.93–0.88 (3H, m). $^{13}$C-NMR; δ (CD$_3$OD), 176.6, 173.2, 62.7, 53.9, 52.5, 45.4, 35.3, 31.6, 30.6, 27.6, 24.1 and 14.7. IR (refection disc); v$_{max}$ 3318, 2955, 1738, 1661, 1642, 1549, 1530, 1465, 1443, 1352, 1216, 1165, 1104, 1040, 1008 and 879 cm$^{-1}$. LRMS; +ve ion 339 (M+Na), −ve ion 315 (M−H).

EXAMPLE 6

2S-{2R-[(Formyl-hydroxy-amino)methyl]-hexanoylamino}-3-methyl Butyric Acid Cyclopentyl Ester

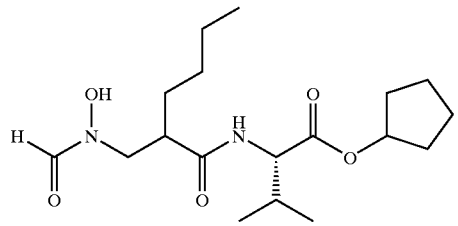

Pale yellow oil. $^1$H-NMR; δ (CD$_3$OD, rotamers), 8.25 (0.4H, s), 7.82 (0.6H, s), 5.19–5.15 (1H, m), 4.24 (1H, d, J=6.3 Hz), 3.81–3.62 (1.4H, m), 3.49–3.38 (0.6H, m), 3.01–2.92 (0.6H, m), 2.81–2.75 (0.4H, m), 2.17–2.00 (1H, m), 1.90–1.34 (14H, m) and 0.95–0.88 (9H, m). $^{13}$C-NMR; δ (CD$_3$OD), 176.6, 173.2, 159.8, 79.7, 60.0, 53.9, 45.8, 45.6, 34.0, 32.0, 31.5, 30.7, 25.0, 24.1, 19.9, 19.1 and 14.7. LRMS; +ve ion 379 (M+Na), –ve ion 355 (M–H).

The compounds of Example 7–10 were prepared by the method of Example 3 by parallel synthesis, using the appropriate amino acid derivative instead of tert-leucine cyclopentyl ester in Step E. The products were purified by preparative HPLC:

EXAMPLE 7

2S-{2R-[(Formyl-hydroxy-amino)-methyl]-hexanolamino}-3-phenyl-propionic Acid Methyl Ester

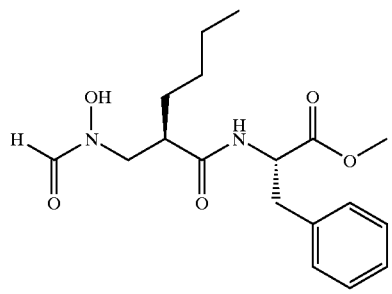

LRMS; +ve ion 373 (M+Na), –ve ion 349 (M–H).

EXAMPLE 8

2S-{2R-[(Formyl-hydroxy-amino)-methyl]-hexanoylamino}-3-phenyl-propionic Acid Ethyl Ester

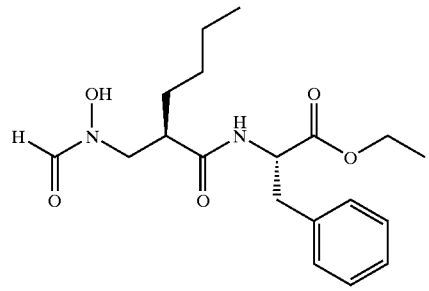

LRMS; +ve ion 387 (M+Na), –ve ion 363 (M–H).

EXAMPLE 9

2S-{2R-[(Formyl-hydroxy-amino)-methyl]-hexanoylamino}-3,3-dimethyl Butyric Acid Iso-propyl Ester

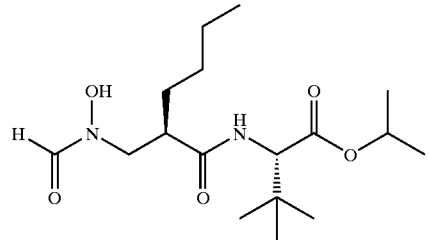

LRMS; +ve ion 367 (M+Na), –ve ion 343 (M–H)

EXAMPLE 10

2R (or S)-{2R-[(Formyl-hydroxy-amino)-methyl]-hexanoylamino}-2-phenyl Acetic Acid Cyclopentyl Ester

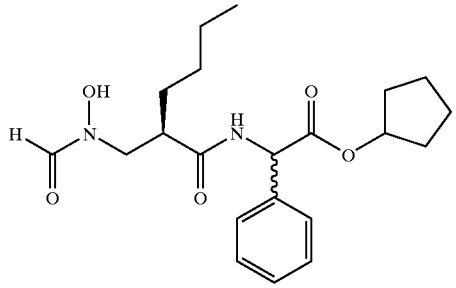

LRMS; +ve ion 413 (M+Na), 391 (M+H), –ve ion 389 (M–H).

Example 11 was prepared by the method of Example 3, by using the appropriate amino acid derivative instead of tert-leucine cyclopentyl ester in step E:

EXAMPLE 11

2S-{2R-[(Formyl-hydroxy-amino)-methyl]-hexanoylamino}-3,3-dimethyl-butyric Acid Tert-butyl Ester

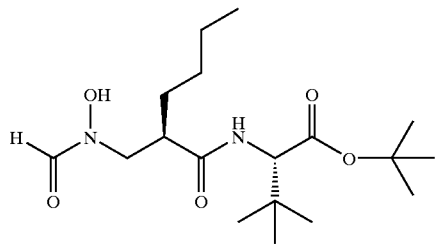

m.p. 76.1–78.2° C. $^1$H-NMR; δ CDCl$_3$, rotamers), 8.37 (0.4H, s), 7.80 (0.6H, s), 6.42 (0.4H, d, J=9.3 Hz), 6.29 (0.6H, d, J=9.5 Hz), 4.33 (1H, d J=9.5 Hz), 3.98 (0.4H, dd, J=14.6, 7.3 Hz), 3.85 (0.6H, dd, J=14.1, 9.6 Hz), 3.64 (0.4H, dd, J=14.6, 3.5 Hz), 3.45 (0.6H, dd, J=14.1, 4.2 Hz), 2.85–2.75 (0.6H, m), 2.73–2.66 (0.4H, m), 1.67–1.19 (6H, m), 1.47 (9H, s), 0.99 (3H, s), 0.94 (6H, s) and 0.90–0.85 (3H, m). $^{13}$C-NMR; δ (CDCl$_3$, rotamers) 176.3, 173.1, 170.9, 82.5, 61.2, 61.0, 52.1, 48.4, 46.7, 45.3, 35.0, 30.5, 30.4, 29.7, 29.6, 28.4, 27.0, 22.9 and 14.3. IR (reflection disc); ν$_{max}$ 3405, 2967, 1708, 1680, 1653, 1524, 1474, 1369, 1285, 1238 and 1173 cm-1. LRMS; +ve ion 381 [M+Na], –ve ion 357 [M–1].

The compounds of Examples 12 and 13 were prepared by the method of Example 3 by parallel synthesis, using the appropriate amino acid derivative instead of tert leucine cyclopentyl ester in Step E. The products were purified by preparative HPLC:

EXAMPLE 12

2S-{2R-[(Formyl-hydroxy-amino)-methyl]-hexanoylamino}-3,3-dimethyl-butyric Acid 1-ethyl-propyl Ester

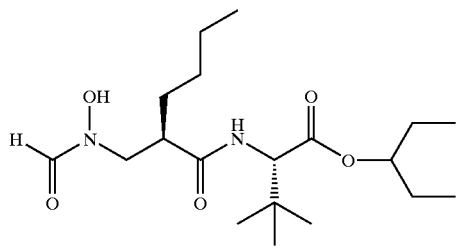

LRMS; +ve ion 373 [M+1], 395 [M+Na], –ve ion 371 [M–1].

EXAMPLE 13

2S-{2R-[(Formyl-hydroxy-amino)-methyl]-hexanoylamino}-3,3-dimethyl-butyric Acid Tetrahydropyran-4-yl Ester

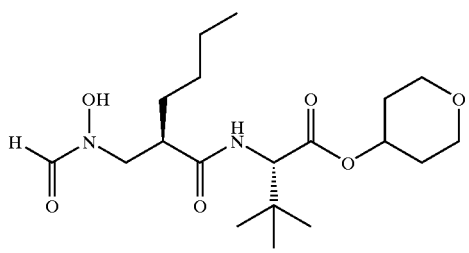

LRMS; +ve ion 387 [M+1], 409 [M+Na], –ve ion 385 [M–1].

The compounds of Examples 14 and 15 were prepared from 2R-(teft-butoxyamino-methyl)-hexanoic acid and the appropriate amino acid derivative by anology with methods described for Example 3:

EXAMPLE 14

2S-{2R-[(Formyl-hydroxy-amino)-methyl]-hexanoylamino}-3-phenyl-propionic Acid Benzyl Ester

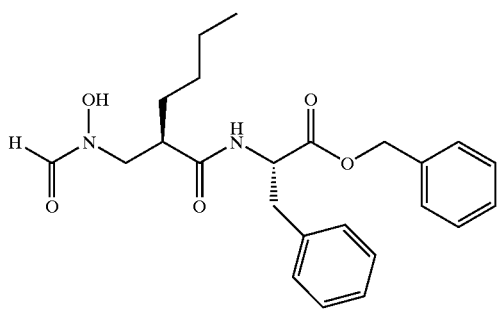

$^1$H-NMR; δ CDCl$_3$, rotamers) 8.33 (0.4H, s), 7.79 (0.6H, s), 7.37–7.21 (8H, m), 7.01–6.98 (2H, m), 6.24–6.15 (1H, m), 5.21–5.07 (2H, m), 4.94–4.84 (1H, m), 3.91 dd, J=14.7, 7.4 Hz), 3.77 (0.6H, dd, J=14.3,9.7 Hz), 3.55 (0.4H, dd, J=14.5, 3.4 Hz), 3.43 (0.6H, dd, J=14.2,4.4 Hz), 3.25–2.98 (2H, m), 2.71–2.64 (0.6H, m), 2.52–2.51 (0.4H, m), 1.56–1.25 (6H, m) and 0.84 (3H, br,s). $^{13}$C-NMR; δ (CDCl$_3$, rotamers) 157.7, 172.5, 171.2, 135.5, 135.3, 135.0, 134.8, 129.3, 129.2, 128.7, 128.6, 127.4, 127.2, 67.7, 67.4, 53.4, 50.8, 48.0, 46.1, 44.6, 38.0, 37.6, 29.9, 29.8, 29.1, 29.0, 22.5 and 13.7. LRMS; +ve ion 427 [M+1], 449 [M+Na].

EXAMPLE 15

2S-{2R-[(Formyl-hydroxy-amino)-methyl]-hexanoylamino}-3,3-dimethyl-butyric Acid Benzyl Ester

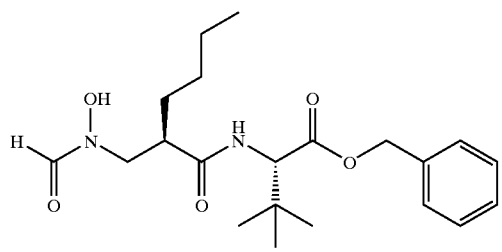

$^1$H-NMR; δ (CDCl$_3$, rotamers) 8.35 (0.2H, s), 7.74 (0.8H, s), 7.35 (5H, s), 6.50 (1H, d, J=9.3 Hz), 5.21–5.15 (2H, m), 4.45 (H, d, J=9.3 Hz), 3.98 (0.2H, dd, J=14.6, 7.4 Hz), 3.82 (0.8H, dd, J=14.1, 9.8 Hz), 3.62 (0.2H, dd, J=14.7, 3.5 Hz), 3.42 (0.8H, dd, J=14.1, 3.9 Hz), 2.88–2.74 (0.8H, m), 2.71–2.63 (0.2H, m), 1.66–1.16 (6H, m), and 0.98–0.83 (12H, m). $^{13}$C-NMR; δ (CDCl$_3$, rotamers) 176.4, 173.4, 171.6, 135.6, 129.0, 128.8, 67.7, 67.4, 60.9, 60.7, 52.6, 48.3, 46.5, 45.0, 35.3, 35.1, 30.5, 30.3, 29.6, 29.5, 27.0, 26.9, 22.9 and 14.3. LRMS; +ve ion 393 [M+1], 415 [M+Na], −ve ion 391 [M−1].

Example 16 was prepared from 3-benzyloxyamino-2R-cyclopentylmethyl-propionic acid and phenylalanine cyclopentyl ester by analogy with methods described in patent number WO 99/39704:

EXAMPLE 16

2S-[2R-Cyclopentylmethyl-3-(formyl-hydroxy-amino)-propionylamino]-3-phenyl-propionic Acid Cyclopentyl Ester

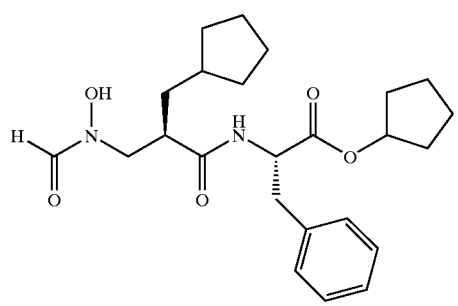

m.p. 76.8–78.5° C. $^1$H-NMR; δ CDCl$_3$, rotamers) 8.34 (0.3H, s), 7.78 (0.7H, s), 7.34–7.09 (5H, m), 6.38–6.33 (1H, m), 5.24–5.19 (0.4H, m), 5.15–5.11 (0.6H, m), 4.83–4.71 (1H, m), 3.91(0.4H, dd, J=14.6, 7.4 Hz), 3.76 (0.6H, dd, J=14.1, 9.5 Hz), 3.55 (0.4H, dd, J=14.6, 3.4 Hz), 3.42 (0.6H, dd, J=14.1, 4.3 Hz), 3.23–2.92 (2H, m), 2.82–2.73 (0.7H, m), 2.58–2.56 (0.3H, m), 1.87–1.27 (17H, m) and 1.05–1.03 (2H, m). $^{13}$C-NMR; δ (CDCl$_3$, rotamers) 176.0, 173.1, 171.7, 171.5, 136.2, 136.1, 129.8, 129.8, 129.6, 129.1, 128.9, 127.7, 127.5, 79.6, 79.0, 53.9, 53.6, 52.4, 48.8, 45.7, 44.4, 38.6, 38.0, 37.9, 37.7, 36.9, 36.8, 33.4, 33.3, 33.0, 32.9, 32.8, 32.7, 25.6, 25.5 and 24.0. IR (reflection disc); V$_{max}$ 3329, 2946, 2864, 1732, 1682, 1644, 1525, 1445, 1345, 1252, 1196 and 881 cm-1. LRMS; +ve ion 431 [M+1], −ve ion 429 [M−1].

EXAMPLES 17–28

Further compounds useful in accordance with the invention are those specifically named and characterised in International patent application WO 99/41232, as follows:

EXAMPLE 17

2S-{2R-[(Formyl-hydroxy-amino)-methyl]-hexanoylamino}-2-phenyl Acetic Acid Ethyl Ester (Example 10 of WO 99/41232.)

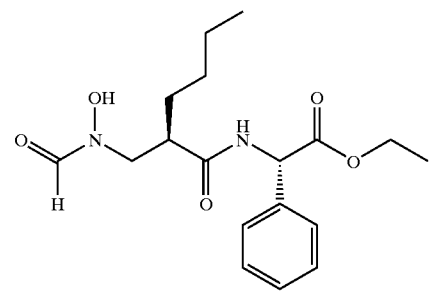

EXAMPLE 18

S-{(2R-[(Formyl-hydroxy-amino)-methyl]-hexanoylamino}-2-phenyl Acetic Acid Iso-propyl Ester (Example 11 of WO 99/41232.)

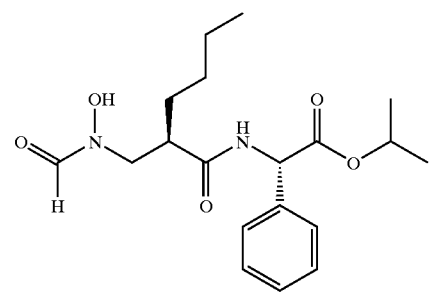

EXAMPLE 19

2S-{2R-[(Formyl-hydroxy-amino)-methyl]-hexanoylamino}-3,3-dimethyl butyric Acid Ethyl Ester (Example 12 of WO 99/41232.)

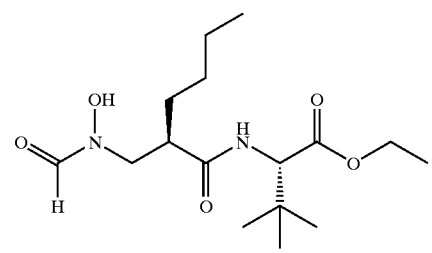

EXAMPLE 20

2S-{2R-[(Formyl-hydroxy-amino)methyl]-hexanoylamino-3,3-dimethyl Butyric Acid Cyclobutyl Ester (Example 14 of WO 99/41232.)

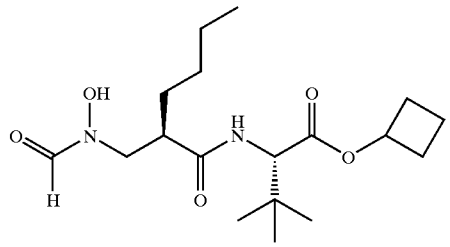

EXAMPLE 21

2S-{2R-[(Formyl-hydroxy-amino)-methyl]-hexanoylamino}3,3-dimethyl Butyric Acid Cyclohexyl Ester (Example 15 of WO 99/41232.)

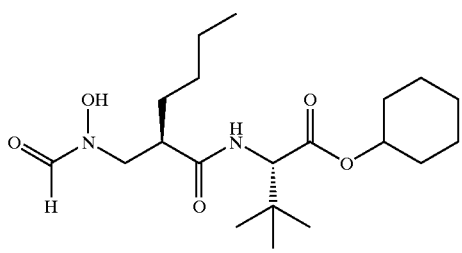

EXAMPLE 22

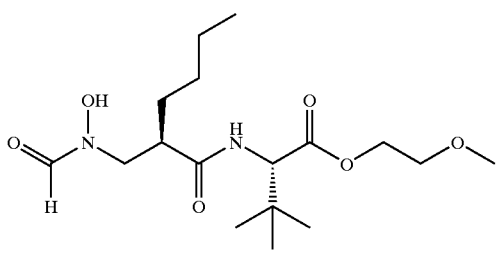

2S-{2R-[(Formyl-hydroxy-amino)-methul] hexanoylamino}-3,3-dimethyl Butyric Acid 2-methoxy-ethyl Ester (xample 16 of WO 99/41232.)

EXAMPLE 23

2S-{2R-[(Formyl-hydroxy-amino)-methyl]-hexanoylamino}-3,3-dimethyl Butyric Acid 1-methyl-piperidin-4-yl Ester (Example 17 of WO 99/41232.)

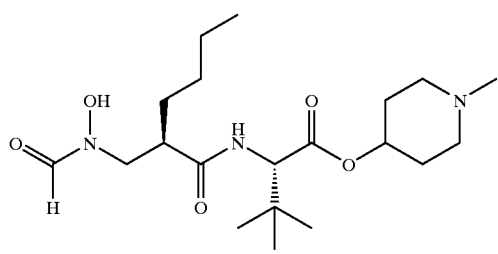

EXAMPLE 24

2S-{2R-[(Formyl-hydroxy-amino)methyl]-hexanoylamino}-3,3-dimethyl Butyric Acid Cyclopentylmethyl Ester (Example 18 of WO 99/41232.)

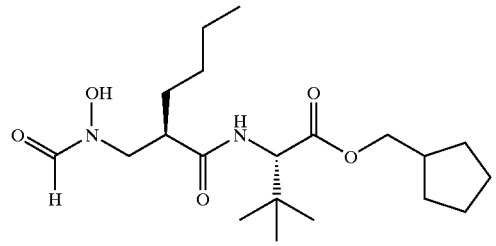

EXAMPLE 25

2S-2R-[(Formyl-hydroxy-amino)-methyl]-hexanoylamino}-3-phenyl-propionic Acid iso-propyl Ester (Example 19 of WO 99/41232.)

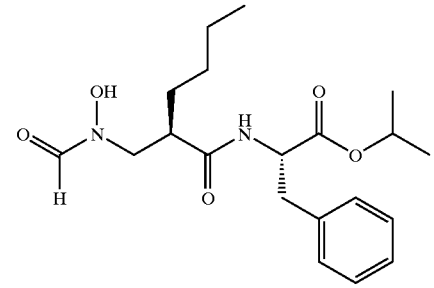

EXAMPLE 26

S-{2R-[(Formyl-hydroxy-amino)-methyl]-hexanoylamino}-2-phenyl Acetic Acid Methyl Ester (Example 20 of WO 99/41232.)

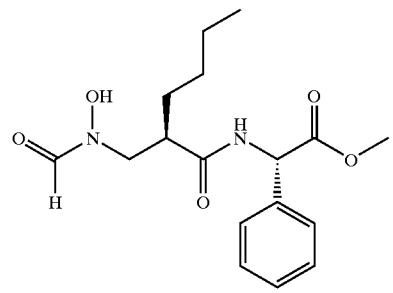

EXAMPLE 27

S-{2R-[Formyl-hydroxy-amino)-methyl]-hexanoylamino}-2-phenyl Acetic Acid Tert-butyl Ester (Example 21 of WO 99/41232.)

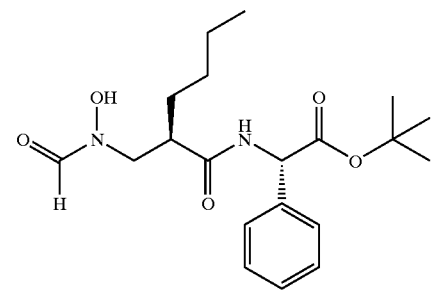

EXAMPLE 28

2S-{2R-[Formyl-hydroxy-amino)-methyl]-hexanoylamino}-3-phenyl-propionic Acid Tert-butyl Ester (Example 22 of WO 99/41232.)

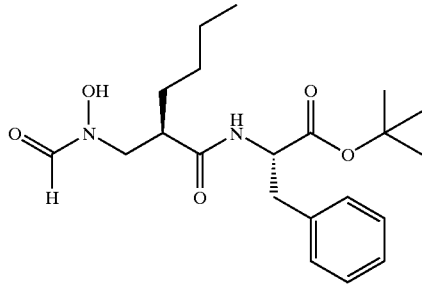

Biological Example

Minimal inhibitory concentrations (MIC) of inhibitors against *E. coli* strain DH5α (Genotype; F-_φ80d/acZΔM15Δ (lacZYA-argF)U169 deoR recA1 endA1 hsdR$_{17}$($r_k^-$,$m_k^+$) phoA supE44λ$^-$thi-1 gyrA96 re/A1) obtained from Gibco-BRL Life Technologies, or *Staphylococcus capitis* (American Type Culture Collection number 35661) were determined as follows. Stock solutions of each test compound were prepared by dissolution of the compound in dimethylsulfoxide at 10 mM. For the determination of the minimal inhibitory concentration, two fold serial dilutions were prepared in 2×YT broth (typtone-16 g/l, yeast extract 10 g/l, sodium chloride 5 g/l obtained from BIO 101 Inc, 1070 Joshua Way, Vista, Calif. 92083, USA) to yield 0.05 ml compound-containing medium per well. Inocula were prepared from cultures grown overnight in 2×YT broth at 37° C. Cell densities were adjusted to absorbance at 660 nm ($A_{660}$)=0.1; the optical density-standardized preparations were diluted 1:1000 in 2×YT broth; and each well inoculated with 0.05 ml of the diluted bacteria. Microtiter plates were incubated at 37° C. for 18 hours in a humidified incubator. The MIC (μM) was recorded as the lowest drug concentration that inhibited visible growth. Examples of results obtained for some of the compounds of the examples above are shown in the following Table

| | MIC μM | |
|---|---|---|
| Compound | *Escherichia coli* | *Staphylococcus capitis* |
| Example 1 | 500 | 12.5 |
| Example 2 | >200 | 200–300 |
| Example 3 | 50 | 12.5 |
| Example 4 | 200–300 | 25 |
| Example 5 | 50 | 200 |
| Example 6 | 100 | 50 |

What is claimed is:

1. A method for the treatment of bacterial infections in humans and non-human mammals, which comprises administering to a subject suffering such infection an antibacterially effective dose of an antibacterial pharmaceutical or veterinary composition comprising a compound of formula (I) or a pharmaceutically or veterinarily acceptable salt, hydrate or solvate thereof, and a pharmaceutically or veterinarily acceptable excipient or carrier:

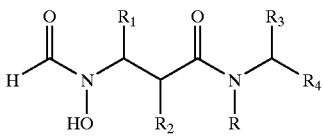

wherein $R_1$ represents hydrogen, $C_1$–$C_6$ alkyl or $C_1$–$C_6$ alkyl substituted by one or more halogen atoms;

$R_2$ represents a group $R_{10}$—(X)$_n$—(ALK)— wherein
$R_{10}$ represents hydrogen, a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo, trifluoromethyl, cyano, nitro, —COOH, —CONH$_2$, —COOR$^A$, —NHCOR$^A$, —CONHR$^A$, —NHR$^A$, —NR$^A$R$^B$, or —CONR$^A$R$_B$ wherein R$_A$ and R$_B$ are independently a ($C_1$–$C_6$)alkyl group, and ALK represents a straight or branched divalent $C_1$–$C_6$ alkylene, $C_2$–$C_6$ alkenylene, or $C_2$–$C_6$ alkynylene radical, which may be interrupted by one or more non-adjacent —NH—, —O— or —S— linkages, X represents —NH—, —O— or —S—, and n is 0 or 1;

R represents hydrogen or $C_1$–$C_6$ alkyl, $R_3$ represents the characterising group of a natural or non-natural α amino acid in which any functional groups may be protected; and $R_4$ represents an ester or thioester group.

2. The method as claimed in claim 1 wherein the stereochemical configuration at the carbon atom carrying the $R_2$ group is R.

3. The method as claimed in claim 1 wherein $R_1$ is hydrogen.

4. The method as claimed in claim 1 wherein $R_2$ is:

$C_1$–$C_6$ alkyl, $C_3$–$C_6$alkenyl or $C_3$–$C_6$alkynyl;

phenyl($C_1$–$C_6$ alkyl)-, phenyl($C_3$–$C_6$alkenyl)- or phenyl($C_3$–$C_6$alkynyl)- optionally substituted in the phenyl ring;

cycloalkyl($C_1$–$C_6$ alkyl)-, cycloalkyl($C_3$–$C_6$alkenyl)- or cycloalkyl($C_3$–$C_6$alkynyl)- optionally substituted in the phenyl ring;

heterocyclyl($C_1$–$C_6$ alkyl)-, heterocyclyl($C_3$–$C_6$alkenyl)- or heterocyclyl($C_3$–$C_6$alkynyl)- optionally substituted in the heterocyclyl ring; or 4-phenylphenyl($C_1$–$C_6$ alkyl)-, 4-phenylphenyl($C_3$–$C_6$alkenyl)-, 4-phenylphenyl($C_3$–$C_6$alkynyl)-, 4-heteroarylphenyl($C_1$–$C_6$ alkyl)-, 4-heteroarylphenyl($C_3$–$C_6$alkenyl)-, 4-heteroarylphenyl($C_3$–$C_6$alkynyl)-, optionally substituted in the terminal phenyl or heteroaryl ring.

5. The method claimed in claim 3 wherein $R_2$ is methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2- ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

6. The method as claimed in claim 3 wherein $R_2$ is n-propyl, n-butyl, n-pentyl, benzyl or cyclopentylmethyl.

7. The method as claimed in claim 4 wherein R is hydrogen.

8. The method as claimed in claim 7 wherein $R_3$ is:

$C_1$–$C_6$ alkyl, phenyl, 2-, 3-, or 4-hydroxyphenyl, 2-,3-, or 4-methoxyphenyl, 2-,3-, or 4-pyridylmethyl, benzyl, 2-,3-, or 4-hydroxybenzyl, 2-,3-, or 4-benzyloxybenzyl, 2-,3-, or 4- $C_1$–$C_6$ alkoxybenzyl, or benzyloxy($C_1$–$C_6$ alkyl)-; or $C_1$–$C_6$ alkyl, phenyl, 2-,3-, or 4-hydroxyphenyl, 2-,3-, or 4-methoxyphenyl, 2-,3-, or 4-pyridylmethyl, benzyl, 2-,3-, or 4-hydroxybenzyl, 2-,3-, or 4-benzyloxybenzyl, 2-,3-, or 4-$C_1$–$C_6$ alkoxybenzyl, or benzyloxy($C_1$–$C_6$ alkyl)-; or the characterising group of a natural α amino acid, in which any functional group may be protected, any amino group may be acylated and any carboxyl group present may be amidated; or a group —Alk$)_n$$R_7$ where Alk is a ($C_1$–$C_6$)alkyl or ($C_2$–$C_6$)alkenyl group optionally interrupted by one or more —O—, or —S— atoms or —N($R_{12}$)- groups, where $R_{12}$ is a hydrogen atom or a ($C_1$–$C_6$)alkyl group, n is 0 or 1, and $R_7$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:

each of R$_a$, R$_b$ and R$_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or R$_c$ is hydrogen and R$_a$ and R$_b$ are independently phenyl or heteroaryl such as pyridyl; or R$_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring; or R$_a$ and R$_b$ are each independently ($C_1$–$C_6$)alkyl, ($C_2$–$C_6$)alkenyl, ($C_2$–$C_6$)alkynyl, phenyl($C_1$–$C_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$) alkyl, —S($C_2$–$C_6$) alkenyl, —SO($C_2$–$C_6$)alkenyl, —SO$_2$($C_2$–$C_6$) alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO H, —CO$_2$($C_1$–$C_6$)alkyl, —CONH$_2$, —CONH($C_1$–$C_6$) alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$)alkyl, —NO$_2$, —NH$_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl or benzyl.

9. The method as claimed in claim 7 wherein $R_3$ is methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, or 4-aminobutyl.

10. The method as claimed in claim 7 wherein $R_3$ is methyl, benzyl, tert-butyl, iso-butyl, phenyl or isopropyl.

11. The method as claimed in claim 8 wherein $R_4$ is a group of formula —(C=O)O R$_9$, —(C=O)SR$_9$, —(C=S)S R$_9$, and —(C=S)O R$_9$ wherein R$_9$ is ($C_1$–$C_6$)alkyl, ($C_2$–$C_6$) alkenyl, cycloalkyl, cycloalkyl($C_1$–$C_6$)alkyl-, phenyl, heterocyclyl, phenyl($C_1$–$C_6$)alkyl-, heterocyclyl($C_1$–$C_6$) alkyl-, ($C_1$–$C_6$)alkoxy($C_1$–$C_6$)alkyl-, or ($C_1$–$C_6$)alkoxy ($C_1$–$C_6$)alkoxy($C_1$–$C_6$)alkyl-, any of which may be substituted on a ring or non-ring carbon atom or on a ring heteroatom, if present.

12. The method as claimed in claim 11 wherein $R_4$ is a group of formula —(C=O)OR$_9$ wherein R$_9$ is methyl, ethyl, n-or iso-propyl, n-, sec- or tert-butyl, 1-ethyl-prop-1-yl, 1-methyl-prop-1-yl, 1-methyl-but-1-yl, cyclopentyl, cyclohexyl, allyl, phenyl, benzyl, 2-,3- and 4-pyridylmethyl, N-methylpiperidin-4-yl, 1- methylcyclopent-1yl, adamantyl, tetrahydrofuran-3-yl or methoxyethyl.

13. The method as claimed in claim 11 wherein $R_4$ is a group of formula —(C=O)OR$_9$ wherein R$_9$ is benzyl, cyclopentyl, isopropyl or tert-butyl.

14. The method as claimed in claim 1 wherein R and $R_1$ are each hydrogen, $R_2$ is n-propyl, n-butyl, n-pentyl, benzyl or cyclopentylmethyl, $R_3$ is methyl, benzyl, tert-butyl, iso-butyl, phenyl or isopropyl, and wherein the stereochemical configuration at the carbon atom carrying the $R_2$ group is R.

15. The method as claimed in claim 1 wherein the compound of formula (I) is selected from the group consisting of:

2S-[2-(R,S)-Benzyl-3-(formyl-hydroxy-amino)-propionylamino]-3-phenyl-propionic acid cyclopentyl ester;

2S-{2R-[1-(R,S)-(Formyl-hydroxy-amino)-ethyl]-4-methyl-pentanoylamino}-3-phenylpropionic acid cyclopentyl ester;

2S-{2R-[(Formyl-hydroxy-amino)-methyl]-hexanoylamino}-3,3-dimethyl butyric acid cyclopentyl ester;

2S-{2R-[(Formyl-hydroxy-amino)-methyl]-hexanoylamino}-3-phenyl-propionic acid cyclopentyl ester;

2S-{2R-[(Formyl-hydroxy-amino)-methyl]-hexanoylamino}-3,3-dimethyl butyric acid methyl ester;

2S-{2R-[(Formyl-hydroxy-amino)-methyl]-hexanoylamino}-3-methyl butyric acid cyclopentyl ester;

2S-{2R-[(Formyl-hydroxy-amino)-methyl]-hexanoylamino}-3-phenyl-propionic acid methyl ester;

2S-{2R-[(Formyl-hydroxy-amino)-methyl]-hexanoylamino}-3-phenyl-propionic acid ethyl ester;

2S-{2R-[(Formyl-hydroxy-amino)-methyl]-hexanoylamino}-3,3-dimethyl butyric acid iso-propyl ester;

2R (or S)-{2R-[(Formyl-hydroxy-amino)-methyl]-hexanoylamino}-2-phenyl acetic acid cyclopentyl ester;

2S-{2R-[(Formyl-hydroxy-amino)-methyl]-hexanoylamino}-3,3-dimethyl-butyric acid tert-butyl ester;

2S-{2R-[(Formyl-hydroxy-amino)-methyl]-hexanoylamino}-3,3-dimethyl-butyric acid 1-ethyl-propyl ester;

2S-{2R-[(Formyl-hydroxy-amino)-methyl]-hexanoylamino}-3,3-dimethyl-butyric acid tetrahydro-pyran-4-yl ester;

2S-{2R-[(Formyl-hydroxy-amino)-methyl]-hexanoylamino}-3-phenyl-propionic acid benzyl ester;

2S-{2R-[(Formyl-hydroxy-amino)-methyl]-hexanoylamino}-3,3-dimethyl-butyric acid benzyl ester;

2S-[2R-Cyclopentylmethyl-3-(formyl-hydroxy-amino)-propionylamino]-3-phenyl-propionic acid cyclopentyl ester;

2S-{2R-[(Formyl-hydroxy-amino)-methyl]-hexanoylamino}-2-phenyl acetic acid ethyl ester;

S-{2R-[(Formyl-hydroxy-amino)-methyl]-hexanoylamino}-2-phenyl acetic acid iso-propyl ester;

2S-{2R-[(Formyl-hydroxy-amino)-methyl]-hexanoylamino}-3,3-dimethyl butyric acid ethyl ester;

2S-{2R-[(Formyl-hydroxy-amino)-methyl]-hexanoylamino}-3,3-dimethyl butyric acid cyclobutyl ester;

2S-{2R-[(Formyl-hydroxy-amino)-methyl]-hexanoylamino}-3,3-dimethyl butyric acid cyclohexyl ester;

2S-{2R-[(Formyl-hydroxy-amino)-methyl]-hexanoylamino}-3,3-dimethyl butyric acid 2-methoxy-ethyl ester;

2S-{2R-[(Formyl-hydroxy-amino)-methyl]-hexanoylamino}-3,3-dimethyl butyric acid 1-methyl-piperidin-4-yl ester;

2S-{2R-[(Formyl-hydroxy-amino)-methyl]-hexanoylamino}-3,3-dimethyl butyric acid cyclopentylmethyl ester;

2S-{2R-[(Formyl-hydroxy-amino)-methyl]-hexanoylamino}-3-phenyl-propionic acid iso-propyl ester;

S-{2R-[(Formyl-hydroxy-amino)-methyl]-hexanoylamino}-2-phenyl acetic acid methyl ester;

S-{2R-[(Formyl-hydroxy-amino)-methyl]-hexanoylamino}-2-phenyl acetic acid tert-butyl ester; and 2S-{2R-[(Formyl-hydroxy-amino)-methyl]-hexanoylamino}-3-phenyl-propionic acid tert-butyl ester.

\* \* \* \* \*